(12) United States Patent
Aebi et al.

(10) Patent No.: US 8,912,221 B2
(45) Date of Patent: Dec. 16, 2014

(54) BIARYL AMIDE DERIVATIVES

(75) Inventors: Johannes Aebi, Binningen (CH); Alfred Binggeli, Binningen (CH); Cornelia Hertel, Brislach (CH); Anish Ashok Konkar, Binningen (CH); Holger Kuehne, Loerrach (DE); Bernd Kuhn, Reinach (CH); Hans P. Maerki, Basel (CH); Haiyan Wang, Allschwil (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 45 days.

(21) Appl. No.: 13/329,349

(22) Filed: Dec. 19, 2011

(65) Prior Publication Data

US 2012/0165338 A1   Jun. 28, 2012

(30) Foreign Application Priority Data

Dec. 27, 2010 (EP) .................................... 10197030

(51) Int. Cl.
| | | |
|---|---|---|
| A61K 31/443 | (2006.01) | |
| C07D 413/14 | (2006.01) | |
| C07D 405/14 | (2006.01) | |
| C07D 413/12 | (2006.01) | |
| C07D 405/12 | (2006.01) | |
| C07D 305/08 | (2006.01) | |
| C07D 417/14 | (2006.01) | |

(52) U.S. Cl.
CPC ............ C07D 413/12 (2013.01); C07D 405/14 (2013.01); C07D 405/12 (2013.01); C07D 305/08 (2013.01); C07D 413/14 (2013.01); C07D 417/14 (2013.01)
USPC ........................................ 514/340; 546/269.1

(58) Field of Classification Search
USPC ........................................ 546/269.1; 514/340
See application file for complete search history.

(56) References Cited

FOREIGN PATENT DOCUMENTS

| WO | 2004/019868 | 11/2004 |
|----|-------------|---------|
| WO | 2010/097372 | 2/2010 |
| WO | 2010/097374 | 2/2010 |

OTHER PUBLICATIONS

Dorwald, Side Reactions in Organic Synthesis, 2005, Wiley: VCH Weinheim Preface, pp. 1-15 & Chapter 8, pp. 279-308.*
Goodman et al., "The Pharmacological Basis of Therapeutics" 7:35-48 (1985).
"International Search Report PCT/EP2011/073717 mailed Mar. 14, 2012".
The English translation of the Chinese Office Action, issued on Jun. 25, 2014, in the corresponding Chinese application No. 201180059302.0.

\* cited by examiner

*Primary Examiner* — Patricia L Morris

(57) ABSTRACT

The invention provides novel compounds having the general formula (I)

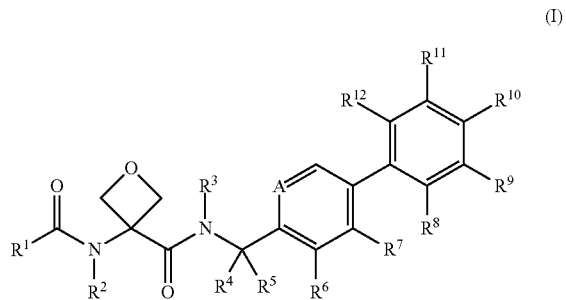

wherein $R^1$, $R^2$, $R^3$, $R^4$, $R^5$, $R^6$, $R^7$, $R^8$, $R^9$, $R^{10}$, $R^{11}$, $R^{12}$ and A are as described herein, compositions including the compounds and methods of using the compounds.

5 Claims, No Drawings

BIARYL AMIDE DERIVATIVES

PRIORITY TO RELATED APPLICATIONS

This application claims the benefit of European Patent Application No. 10197030.9, filed Dec. 27, 2010, which is hereby incorporated by reference in its entirety.

FIELD OF THE INVENTION

The present invention relates to organic compounds useful for therapy or prophylaxis in a mammal, and in particular to bradykinin B1-receptor (BDKRB1 or B1R) antagonists or inverse agonists for the treatment or prophylaxis of glomerulonephritides, Henoch-Schönlein purpura nephropathy (HSPN), ANCA-associated crescentic glomerulonephritis, lupus nephritis and IgA nephritis.

BACKGROUND OF THE INVENTION

Kinins, belong to a family of bioactive octo- to decapeptides generated from the inactive precursor kininogen in a stepwise proteolytic process in body fluids and tissues. Kinins are hormones formed by a group of 9-11 amino acid peptides, including bradykinin (BK), kallidin (KD/Lys-BK), and their active metabolites (des-Arg$^9$-BK and des-Arg$^{10}$-kallidin/Lys-des-Arg$^9$-BK). The kinins play an important physiological role in inflammatory and nociceptive processes. The biological effects of BK and other kinins are mediated by two physiologically distinct G protein-couple receptors (GPCRs), termed BDKRB1 (B1R) and BDKRB2 (B2R). It is believed that under physiological conditions, the constitutively expressed B2R mediates the effects of circulating or locally generated kinins, since B1R is not expressed in normal tissues. The B2R is constitutively expressed in numerous cell types of the central and peripheral nervous systems, the vascular endothelium and inflammatory cells, and is activated by the short lived natural ligands, BK and kallidin (KD). Once synthesized, BK causes vasodilatation and increased vascular permeability by interaction with B2Rs. However, B2Rs are rapidly desensitized and internalized following binding and activation by the endogenous ligands. Catalytic degradation of kinins by enzymes including carboxypeptidase N and carboxypeptidase M yields des-Arg$^9$-BK (DABK) and des-Arg$^{10}$-kallidin/Lys-des-Arg$^9$-BK, which preferentially activate the B1R. Although not expressed in normal tissues (or expressed at very low levels), the B1R is rapidly induced following bacterial infections, tissue injury and release of inflammatory mediators, and has been observed in sympathetic neurons, macrophages, fibroblasts, smooth muscle cells, and the vascular endothelium. The endogenous B1R agonists, including des-Arg$^9$-BK and des-Arg$^{10}$-kallidin/Lys-des-Arg$^9$-BK, are relatively long-lasting peptides. Moreover, the B1R does not undergo rapid desensitization and internalization after stimulation. Once upregulated, B1R activity persists in damaged or inflamed tissues and thought to participate in prolonging the pathological response to kinins. Thus, the B1R has been implicated in maintaining chronic pain, vasodilation, plasma extravasation, neutrophil recruitment and further release of inflammatory mediators, such as IL-1β, TNF-α and IL-6 which sustain a positive feedback loop between B1R expression and inflammation. The proposed upregulation of B1R only under pathological conditions, including inflammation, trauma, burns, shock, and allergy, makes B1R a particularly attractive drug target.

The proposed role of kinins in mediating pain and inflammation has propelled interest in the discovery of potent and selective BK antagonists. Recent evidence suggests that bradykinin receptors may also play an important role in a number of pathological processes or diseases, including ischemia-reperfusion injury, diabetic retinopathy, atherosclerosis, renal disease. Hence, there is an urgent need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools.

As described herein, the compounds of formula (I) are antagonists or inverse agonists of the bradykinin-receptor, in particular the bradykinin B1-receptor (B1R), and as such are useful in the treatment and prevention of diseases and conditions mediated through the stimulation of bradykinin receptor pathway such as pain, inflammation, vasodilation, plasma extravasation, neutrophil recruitment, macrophage infiltration and further release of inflammatory mediators, such as IL-1β and TNF-α.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of glomerulonephritides, Henoch-Schönlein purpura nephropathy (HSPN), ANCA-associated crescentic glomerulonephritis, lupus nephritis and IgA nephritis and the use of the said compounds, salts or esters for the production of medicaments for the treatment or prophylaxis of glomerulonephritides, Henoch-Schönlein purpura nephropathy (HSPN), ANCA-associated crescentic glomerulonephritis, lupus nephritis and IgA nephritis.

SUMMARY OF THE INVENTION

The present invention relates to compounds according to formula (I)

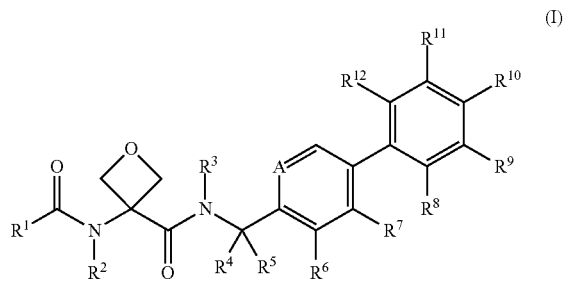

wherein

R$^1$ is selected from the group consisting of alkyl, cycloalkyl, cycloalkylalkyl, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;

$R^2$ is selected from the group consisting of hydrogen, alkyl and cycloalkyl;

$R^3$ is selected from the group consisting of hydrogen, alkyl and cycloalkyl;

$R^4$ is selected from the group consisting of hydrogen, alkyl and cycloalkyl;

$R^5$ is selected from the group consisting of hydrogen, alkyl and cycloalkyl;

or $R^4$ and $R^5$ together form a cycloalkyl with the carbon they are attached to;

$R^6$ is selected from the group consisting of hydrogen, alkyl, alkoxy, cycloalkyl, halogen and cyano;

$R^7$ is selected from the group consisting of hydrogen, alkyl, alkoxy, cycloalkyl, halogen and cyano;

$R^8$ is selected from the group consisting of alkyl, cycloalkyl, cycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy, halocycloalkoxyalkyl, alkoxycarbonyl, cycloalkoxycarbonyl, haloalkoxycarbonyl, halocycloalkoxycarbonyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, alkoxy, alkoxyalkyl, haloalkoxy, alkoxyalkoxy, alkoxyalkoxyalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;

$R^9$ is selected from the group consisting of hydrogen, alkyl, alkoxy, cycloalkyl, halogen and cyano;

$R^{10}$ is selected from the group consisting of hydrogen, alkyl, alkoxy, cycloalkyl, halogen and cyano;

$R^{11}$ is selected from the group consisting of hydrogen, alkyl, alkoxy, cycloalkyl, halogen and cyano;

$R^{12}$ is selected from the group consisting of hydrogen, alkyl, alkoxy, cycloalkyl, halogen and cyano;

$R^{13}$ is selected from the group consisting of hydrogen, alkyl, alkoxy, cycloalkyl, halogen and cyano; and A is $CR^{13}$ or N;

and pharmaceutically acceptable salts thereof.

The present invention also relates to pharmaceutical compositions comprising such a compound and a therapeutically inert carrier.

DETAILED DESCRIPTION OF THE INVENTION

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "antagonist" denotes a compound that diminishes or prevents the action of another compound or receptor site as defined e.g. in Goodman and Gilman's "The Pharmacological Basis of Therapeutics, 7th ed." in page 35, Macmillan Publ. Company, Canada, 1985. In particular, antagonists refers to a compound that attenuates the effect of an agonist. A "competitive antagonist" binds to the same site as the agonist but does not activate it, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy and ethoxy. More particular alkoxy group is methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl and ethoxypropyl. Particular alkoxyalkyl group include methoxymethyl and methoxyethyl. More particular alkoxyalkyl group is methoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy or ethoxy. Particular alkoxycarbonyl group is a group of the formula —C(O)—R', wherein R' is methoxy.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl groups include methyl or ethyl. More particular alkyl group is methyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkoxycarbonyl" denotes a group of the formula —C(O)—R', wherein R' is a cycloalkoxy group. Examples of cycloalkoxycarbonyl groups include groups of the formula —C(O)—R', wherein R' is cyclopropoxy, cyclobutoxy, cyclopentyloxy, cyclohexyloxy, cycloheptyloxy and cyclooctyloxy. Particular cycloalkoxycarbonyl group is a group of the formula —C(O)—R', wherein R' is cyclopropoxy.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy. More particular haloalkoxy group is 2,2-difluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl.

The term "haloalkoxycarbonyl" denotes a group of the formula —C(O)—R', wherein R' is an haloalkoxy group. Examples of haloalkoxycarbonyl groups include a group of the formula —C(O)—R', wherein R' is fluoromethoxy, difluoromethoxy, trifluoromethoxy, trifluoroethoxy, trifluoromethylethoxy, trifluorodimethylethoxy or pentafluoroethoxy.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkoxy" denotes a cycloalkoxy group wherein at least one of the hydrogen atoms of the cycloalkoxy group has been replaced by same or different halogen atoms, particularly fluoro atoms. Examples of halocycloalkoxyl include fluorocyclopropoxy, difluorocyclopropoxy, fluorocyclobutoxy and difluorocyclobutoxy.

The term "halocycloalkoxyalkyl" denotes an alkyl group wherein at least one of the hydrogen atoms of the alkyl group has been replaced by a halocycloalkoxy. Examples of halocycloalkoxyalkyl include fluorocyclopropoxymethyl, difluorocyclopropoxymethyl, fluorocyclopropoxyethyl, difluorocyclopropoxyethyl, fluorocyclobutoxymethyl, difluorocyclobutoxymethyl, fluorocyclobutoxyethyl and difluorocyclobutoxyethyl.

The term "halocycloalkoxycarbonyl" denotes a group of the formula —C(O)—R', wherein R' is an halocycloalkoxy group. Examples of halocycloalkoxycarbonyl groups include groups of the formula —C(O)—R', wherein R' is fluorocyclopropoxymethyl, difluorocyclopropoxymethyl, fluorocyclopropoxyethyl, difluorocyclopropoxyethyl, fluorocyclobutoxymethyl, difluorocyclobutoxymethyl, fluorocyclobutoxyethyl and difluorocyclobutoxyethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, isoxazolyl and isothiazolyl. More particular heteroaryl groups include imidazolyl, oxazolyl, thiazolyl, oxadiazolyl, thiadiazolyl, tetrazolyl, pyridinyl, pyrazinyl, pyrazolyl, pyridazinyl, pyrimidinyl, isoxazolyl and isothiazolyl. Further particular examples of heteroaryl groups in the definition of $R^1$ substituent include imidazolyl, oxadiazolyl, thiadiazolyl, pyridinyl, pyridazinyl, pyrimidinyl and isoxazolyl. Further particular examples of heteroaryl groups in the definition of $R^8$ substituent include oxadiazolyl and tetrazolyl.

The term "hydroxy" denotes a —OH group.

The term "hydroxyalkoxy" an alkoxy group wherein at least one of the hydrogen atoms of the alkoxy group has been replaced by a hydroxy group. Examples of hydroxyalkoxy include hydroxyethoxy, hydroxypropoxy, hydroxymethylpropoxy and dihydroxypropoxy.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriat point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups is the tert-butoxycarbonyl (Boc) and the benzyloxycarbonyl fluorenylmethoxycarbonyl (Fmoc).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention relates to a compound according to formula (I)

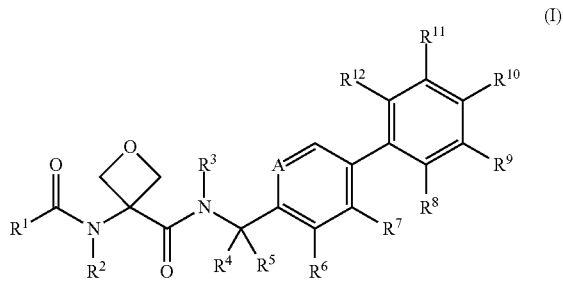

wherein
$R^1$ is selected from the group consisting of alkyl, cycloalkyl, cycloalkylalkyl, alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;
$R^2$ is selected from the group consisting of hydrogen, alkyl and cycloalkyl;
$R^3$ is selected from the group consisting of hydrogen, alkyl and cycloalkyl;
$R^4$ is selected from the group consisting of hydrogen, alkyl and cycloalkyl;
$R^5$ is selected from the group consisting of hydrogen, alkyl and cycloalkyl;
or $R^4$ and $R^5$ together form a cycloalkyl with the carbon they are attached to;
$R^6$ is selected from the group consisting of hydrogen, alkyl, alkoxy, cycloalkyl, halogen and cyano;
$R^7$ is selected from the group consisting of hydrogen, alkyl, alkoxy, cycloalkyl, halogen and cyano;
$R^8$ is selected from the group consisting of alkyl, cycloalkyl, cycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy, halocycloalkoxyalkyl, alkoxycarbonyl, cycloalkoxycarbonyl, haloalkoxycarbonyl, halocycloalkoxycarbonyl, aryl, substituted aryl, heteroaryl and substituted heteroaryl, wherein substituted aryl and substituted heteroaryl are substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, alkoxy, alkoxyalkyl, haloalkoxy, alkoxyalkoxy, alkoxyalkoxyalkyl, amino and substituted amino, wherein substituted amino is substituted with one to two substituents independently selected from the group consisting of alkyl, cycloalkyl, alkylcycloalkyl, cycloalkylalkyl, alkylcycloalkylalkyl, hydroxyalkyl and alkoxyalkyl;
$R^9$ is selected from the group consisting of hydrogen, alkyl, alkoxy, cycloalkyl, halogen and cyano;
$R^{10}$ is selected from the group consisting of hydrogen, alkyl, alkoxy, cycloalkyl, halogen and cyano;
$R^{11}$ is selected from the group consisting of hydrogen, alkyl, alkoxy, cycloalkyl, halogen and cyano;
$R^{12}$ is selected from the group consisting of hydrogen, alkyl, alkoxy, cycloalkyl, halogen and cyano;
$R^{13}$ is selected from the group consisting of hydrogen, alkyl, alkoxy, cycloalkyl, halogen and cyano; and
A is $CR^{13}$ or N;
or a pharmaceutically acceptable salt thereof.

Also an embodiment of the present invention are pharmaceutically acceptable esters of the compounds according to formula (I).

A further embodiment of the present invention are compounds according to formula (I) as described herein, wherein $R^1$ is selected from the group consisting of alkoxyalkyl, cycloalkoxyalkyl, haloalkyl, haloalkoxyalkyl, halocycloalkyl, halocycloalkylalkyl, halocycloalkoxyalkyl, aryl, substituted aryl, heteroaryl and substituted heteroaryl, wherein substituted aryl and substituted heteroaryl are substituted with one to three substituents independently selected from the group consisting of alkyl, cycloalkyl, halogen, haloalkyl, alkoxy, alkoxyalkyl, amino and substituted amino, wherein substituted amino is substituted with one to two substituents independently selected from alkyl and cycloalkyl.

A particular embodiment of the present invention are compounds according to formula (I) as described herein, wherein $R^1$ is selected from the group consisting of alkoxyalkyl, haloalkyl, substituted phenyl, heteroaryl and substituted heteroaryl, wherein substituted phenyl and substituted heteroaryl are substituted with one to three substituents independently selected from the group consisting of alkyl, halogen, haloalkyl, alkoxy and amino.

In a further embodiment of the present invention are compounds according to formula (I) as described herein, wherein $R^1$ is selected from the group consisting of alkoxyalkyl, haloalkyl, imidazolyl, isoxazolyl, oxadiazolyl, thiadiazolyl, pyridinyl, pyridizanyl, and pyrimidinyl, or is selected from the group consisting of phenyl, imidazolyl, isoxazolyl, oxadiazolyl, thiadiazolyl, pyridinyl, pyridizanyl, and pyrimidinyl substituted with one to three substituents independently selected from the group consisting of alkyl, halogen, haloalkyl, alkoxy and amino.

An alternative embodiment of the present invention are compounds according to formula (I) as described herein, wherein $R^1$ is selected from the group consisting of alkoxyalkyl, haloalkyl, isoxazolyl, pyridizanyl, pyrimidinyl, halohaloalkylphenyl, alkylimidazolyl, alkylisoxazolyl, alkoxyisoxazolyl, alkyloxadiazolyl, alkylthiadiazolyl, aminopyridinyl and alkoxypyrimidinyl.

Another embodiment of the present invention are compounds according to formula (I) as described herein, wherein $R^1$ is selected from the group consisting of alkoxyalkyl, haloalkyl, isoxazolyl, pyridizanyl, pyrimidinyl, fluoro-trifluoromethylphenyl, alkylimidazolyl, alkylisoxazolyl, alkoxyisoxazolyl, alkyloxadiazolyl, alkylthiadiazolyl, aminopyridinyl and alkoxypyrimidinyl.

The present invention also relates to compounds according to formula (I) as described herein, wherein $R^1$ is selected from the group consisting of pyridizanyl, alkylisoxazolyl, alkoxyisoxazolyl, alkyloxadiazolyl and alkoxypyrimidinyl.

A particular embodiment of the present invention are compounds according to formula (I) as described herein, wherein $R^8$ is selected from the group consisting of haloalkoxy, alkoxycarbonyl, cycloalkoxycarbonyl, haloalkoxycarbonyl, heteroaryl and substituted heteroaryl, wherein substituted heteroaryl is substituted with one to three alkyl.

A further particular embodiment of the present invention are compounds according to formula (I) as described herein, wherein $R^8$ is selected from the group consisting of haloalkoxy, alkoxycarbonyl and substituted heteroaryl, wherein substituted heteroaryl is substituted with one to three alkyl.

A more particular embodiment of the present invention are compounds according to formula (I) as described herein, wherein $R^8$ is selected from the group consisting of haloalkoxy, alkoxycarbonyl, alkyltetrazolyl and alkyloxadiazolyl.

Also an embodiment of the present invention are compounds according to formula (I) as described herein, wherein $R^8$ is alkyltetrazolyl or alkyloxadiazolyl.

The present invention also relates to compounds according to formula (I) as described herein, wherein $R^2$ is hydrogen.

The present invention also relates to compounds according to formula (I) as described herein, wherein $R^3$ is hydrogen.

Also an embodiment of the present invention are compounds according to formula (I) as described herein, wherein one of $R^4$ and $R^5$ is hydrogen and the other is alkyl.

A particular embodiment of the present invention are compounds according to formula (I) as described herein, wherein one of $R^4$ and $R^5$ is hydrogen and the other is methyl.

Also an embodiment of the present invention are compounds according to formula (I) as described herein, wherein $R^4$ and $R^5$ together form a cycloalkyl with the carbon they are attached to.

The present invention also relates to compounds according to formula (I) as described herein, wherein $R^6$ is hydrogen or halogen.

The present invention also relates to compounds according to formula (I) as described herein, wherein $R^7$ is hydrogen.

The present invention also relates to compounds according to formula (I) as described herein, wherein $R^9$ is hydrogen or halogen.

Also an embodiment of the present invention are compounds according to formula (I) as described herein, wherein $R^{19}$ is hydrogen.

Also an embodiment of the present invention are compounds according to formula (I) as described herein, wherein $R^{11}$ is hydrogen or halogen.

Another embodiment of the present invention are compounds according to formula (I) as described herein, wherein $R^{12}$ is hydrogen.

Another embodiment of the present invention are compounds according to formula (I) as described herein, wherein $R^{13}$ is hydrogen or halogen.

A particular embodiment of the present invention are compounds according to formula (I) as described herein, wherein A is $CR^{13}$.

A particular embodiment of the present invention are compounds according to formula (I) as described herein, wherein A is N.

A further embodiment of the present invention are compounds according to formula (I) as described herein of formula (Ia)

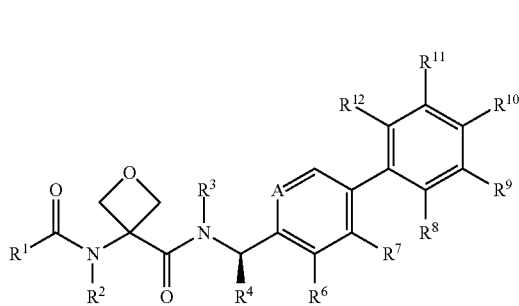

Also a further embodiment of the present invention are compounds according to formula (I) as described herein of formula (Ib)

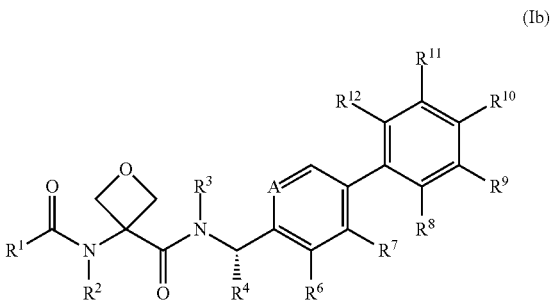

Particular examples of compounds of formula (I) as described herein are selected from the group consisting of 3-(3-Fluoro-5-trifluoromethyl-benzoylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide;

3-(2,2,2-Trifluoro-acetylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide;

Isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-Methyl-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

Pyrimidine-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-Chloro-3'-fluoro-4'-((R)-1-{[3-(2,2,2-trifluoro-acetylamino)-oxetane-3-carbonyl]-amino}-ethyl)-biphenyl-2-carboxylic acid methyl ester;

3-Chloro-3'-fluoro-4'-[(R)-1-({3-[(pyrimidine-5-carbonyl)-amino]-oxetane-3-carbonyl}-amino)-ethyl]-biphenyl-2-carboxylic acid methyl ester;

3-Chloro-3'-fluoro-4'-((R)-1-{[3-(3,3,3-trifluoro-propionylamino)-oxetane-3-carbonyl]-amino}-ethyl)-biphenyl-2-carboxylic acid methyl ester;

3-Methyl-isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

Isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

Pyrimidine-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

3-Chloro-3'-fluoro-4'-[(R)-1-({3-[(isoxazole-5-carbonyl)-amino]-oxetane-3-carbonyl}-amino)-ethyl]-biphenyl-2-carboxylic acid methyl ester;

3-Chloro-3'-fluoro-4'-[(R)-1-({3-[(3-methyl-isoxazole-5-carbonyl)-amino]-oxetane-3-carbonyl}-amino)-ethyl]-biphenyl-2-carboxylic acid methyl ester;

3-Methoxy-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

2-Methoxy-pyrimidine-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

4-Methyl-[1,2,3]thiadiazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-(2-Methoxy-acetylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide;

3-Methoxy-isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

5-Methyl-[1,3,4]oxadiazole-2-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-Methyl-isoxazole-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide;

3-(2,2,2-Trifluoro-acetylamino)-oxetane-3-carboxylic acid ((R)-1-{5-[5-chloro-3-fluoro-2-(2-methyl-2H-tetrazol-5-yl)-phenyl]-3-fluoro-pyridin-2-yl}-ethyl)-amide;

3-(2,2,2-Trifluoro-acetylamino)-oxetane-3-carboxylic acid {(R)-1-[5'-chloro-3,3'-difluoro-2'-(2-methyl-2H-tetrazol-5-yl)-biphenyl-4-yl]-ethyl}-amide;

3-Methyl-isoxazole-5-carboxylic acid (3-{(R)-1-[5'-chloro-3,3'-difluoro-2'-(2-methyl-2H-tetrazol-5-yl)-biphenyl-4-yl]ethylcarbamoyl}-oxetan-3-yl)-amide;

3-Methyl-isoxazole-5-carboxylic acid (3-{(R)-1-[5'-chloro-3,3'-difluoro-2'-(5-methyl-[1,2,4]oxadiazol-3-yl)-biphenyl-4-yl]ethylcarbamoyl}-oxetan-3-yl)-amide;

Pyridazine-4-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

1-Methyl-1H-imidazole-2-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

1-Methyl-1H-imidazole-4-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

5-Amino-N-[3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-nicotinamide;

Pyridazine-3-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

N-[3-((R)-1-{5-[5-Chloro-3-fluoro-2-(5-methyl-[1,2,4]oxadiazol-3-yl)-phenyl]-3-fluoro-pyridin-2-yl}-ethylcarbamoyl)-oxetan-3-yl]-nicotinamide;

2-Methoxy-pyrimidine-5-carboxylic acid (3-{(R)-1-[5'-chloro-3,3'-difluoro-2'-(5-methyl-[1,2,4]oxadiazol-3-yl)-biphenyl-4-yl]ethylcarbamoyl}-oxetan-3-yl)-amide;

Isoxazole-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide;

3-(2,2,2-Trifluoro-acetylamino)-oxetane-3-carboxylic acid {(R)-1-[3',5'-dichloro-2'-(2,2-difluoro-ethoxy)-3-fluoro-biphenyl-4-yl]-ethyl}-amide;

3-Methoxy-isoxazole-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide;

2-Methoxy-pyrimidine-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide;

2-Methoxy-pyrimidine-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide;

3-Methoxy-isoxazole-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide;

5-Methyl-[1,3,4]oxadiazole-2-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide;

5-Methyl-[1,3,4]oxadiazole-2-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

2-Methoxy-pyrimidine-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

4-Methyl-[1,2,3]thiadiazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide;

3-(2-Methoxy-acetylamino)-oxetane-3-carboxylic acid ((R)-1-{5-[3,5-dichloro-2-(2,2-difluoro-ethoxy)-phenyl]-3-fluoro-pyridin-2-yl}-ethyl)-amide;

3-Methoxy-isoxazole-5-carboxylic acid (3-{(R)-1-[5'-chloro-3,3'-difluoro-2'-(2-methyl-2H-tetrazol-5-yl)-biphenyl-4-yl]-ethylcarbamoyl}-oxetan-3-yl)-amide;

2-Methoxy-pyrimidine-5-carboxylic acid (3-{(R)-1-[5'-chloro-3,3'-difluoro-2'-(2-methyl-2H-tetrazol-5-yl)-biphenyl-4-yl]-ethylcarbamoyl}-oxetan-3-yl)-amide;

and pharmaceutically acceptable salts thereof.

Further particular examples of compounds of formula (I) as described herein are selected from the group consisting of 3-Methyl-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-Methoxy-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

2-Methoxy-pyrimidine-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

5-Methyl-[1,3,4]oxadiazole-2-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

3-Methyl-isoxazole-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide;

Pyridazine-3-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;

2-Methoxy-pyrimidine-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
BOP=Benzotriazol-1-yloxytris(dimethylamino)phosphonium hexafluorophosphate
BOP-Cl=Bis(2-oxo-3-oxazolidinyl)phosphinic chloride
DCC=N,N'-Dicyclohexylcarbodiimide
DCM=Dichloromethane
DIC=N,N'-Diisopropylcarbodiimide
DIPEA=Diisopropylethyl amine
DMAP=N,N-Dimethylpyridine
DMF=N,N-Dimethylformamide
DMSO=Dimethylsulfoxide
EDCI=1-(3-Dimethylaminopropyl)-3-ethylcarbodiimide hydrochloride
EtOAc=Ethyl acetate
HATU=O-(7-Azabenzotriazol-1-yl)-1,1,3,3-tetramethyluronium hexafluorophosphate
HOBT=1-Hydroxybenzotriazol
MeOH=Methanol
pTsOH=p-Toluenesulfonic acid
PyBop=(Benzotriazol-1-yloxy)tripyrrolidinophosphonium hexafluorophosphate
TBAF=Tetrabutylammonium fluoride
TBSOTf=tert-Butyldimethylsilyl triflate
TBTU=2-(1H-Benzotriazole-1-yl)-1,1,3,3-tetramethyluronium tetrafluoroborate
TEA=Triethylamine
TFA=Trifluoroacetic acid
THF=Tetrahydrofuran Compounds of formula (I) may be prepared as illustrated in scheme 1 by reacting a compound of general formula (3) with an amine derivative of general formula (2).

Scheme 1

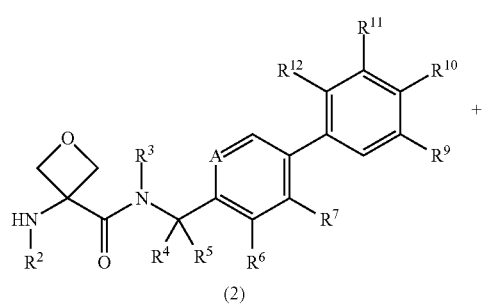

(2)

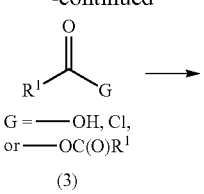

G = ——OH, Cl,
or ——OC(O)R¹

(3)

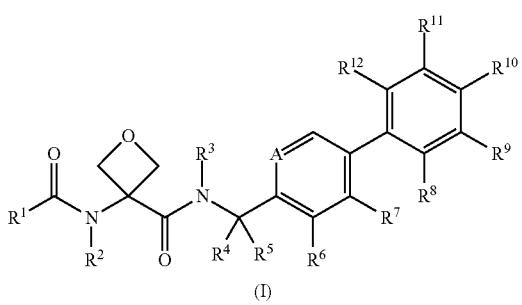

(I)

When using a carboxylic acid of formula (3), wherein G is —OH, this amide coupling step can be performed using standard methods, employing coupling reagents such as EDCI/HOBT, HATU, TBTU, BOP-Cl, BOP, PyBop, DIC/HOBT or DCC/HOBT optionally in presence of a base such as TEA or DIPEA. Alternatively, this amide coupling step can be performed using an acid chloride of formula (3), wherein G is Cl or anhydride of formula (3), wherein G is —OC(O)R¹ in the presence of a base such as TEA, DIPEA or pyridine. Carboxylic acids, acid chlorides or anhydrides of general formula (3) are commercially available or may be prepared from commercially available reagents using standard chemical transformations well known in the art.

Amines of general formula (2) may be prepared as outlined in scheme 2. A suitable protected amine derivative of formula (4), wherein X is halogen, particularly bromo or iodo, wherein PG is a protecting group such as Boc or acetyl, can be converted into the boron ester derivative of formula (5) using bis(pinacolato)diboron in presence of a palladium catalyst and potassium acetate in a polar, aprotic solvent such as DMF or DMSO. Biaryl derivatives of formula (7) can be obtained by coupling of boron ester derivative of formula (5) with arylhalides of formula (6), wherein X is halogen, particularly bromo or iodo, using Suzuki reaction conditions, employing palladium catalysts such as [1,1'-bis(diphenylphosphino)ferrocene]palladium(II) chloride (1:1 complex with DCM), palladium(II) acetate in presence of tri-o-tolyl-phosphine or tetrakis(triphenylphosphine)palladium(0) and a base such as potassium carbonate.

Scheme 2

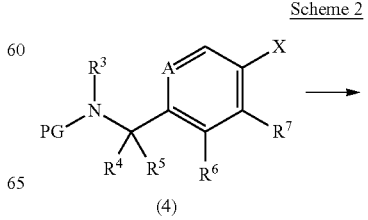

(4)

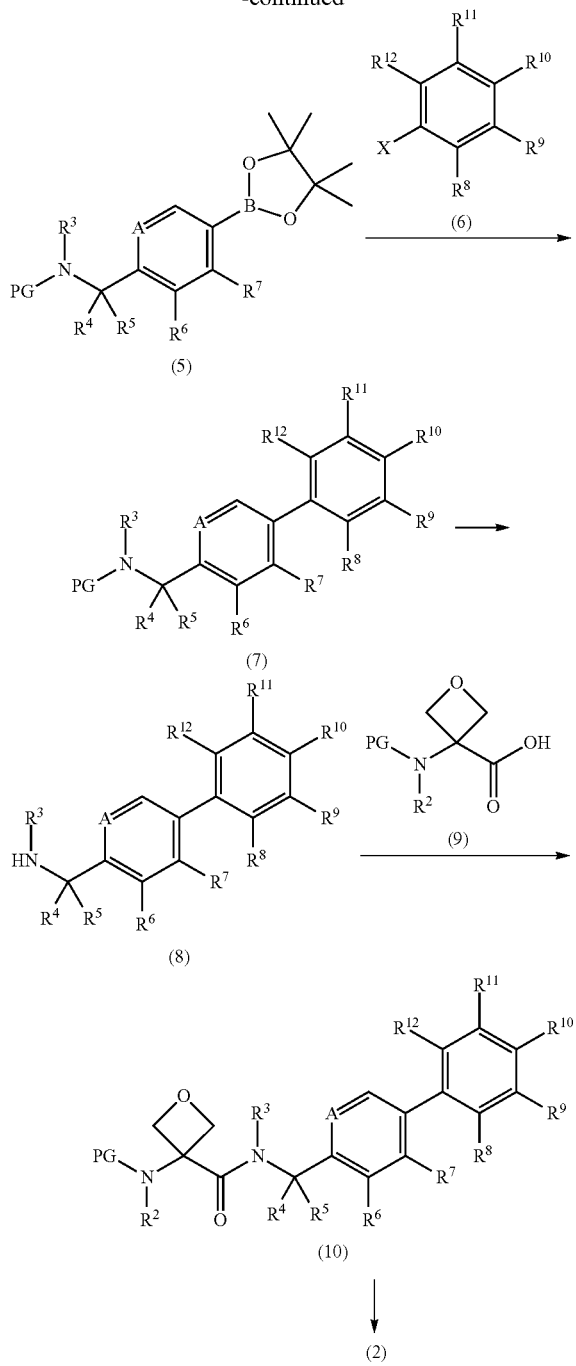

X is halogen particularly, Br or I
PG is e.g. the Boc or the Fmoc protectiong group Depending on the nature of the protecting group, derivatives of formula (7) can be de-protected using appropriate standard conditions, e.g. hydrolysis under acidic conditions employing reagents such as HCl or TFA Amine derivatives of formula (8) can be converted to derivatives of formula (10) by reaction with suitable protected amino-oxetane-carboxylic acid derivatives of formula (9), wherein PG is a protecting group such as Fmoc or Boc, employing coupling reagents such as EDCI/HOBT, HATU, TBTU, BOP-Cl, BOP, PyBop, DIC/HOBT or DCC/HOBT optionally in presence of a base such as TEA or DIPEA. The conversion of derivatives of formula (10) to derivatives of formula (2) amines can be accomplished using standard methods well known to those skilled in the art. For example, in case PG in derivatives of formula (10) is a Fmoc group, this can be removed using a base such as piperidine, morpholine or ammonia. In case PG in derivatives of formula (10) is a Boc group this can be cleaved using a two step procedure employing TBSOTf in the first step and TBAF in the second.

Primary amine derivatives of formula (2), wherein $R^2$ is hydrogen, can be elaborated into secondary amine derivatives of formula (2), wherein $R^2$ is alkyl or cycloalkyl, by N-alkylation with a reagent $R^2$—I or $R^2$—Br in presence of a base such as TEA.

Compounds of general formula (4), wherein X is halogen, particularly bromo or iodo, and wherein PG is a suitable protecting group, are commercially available or may be prepared from commercially available reagents using standard chemical transformations well known in the art. These amines of general formula (4) may be prepared as illustrated in Schemes 3 to 5.

Scheme 3

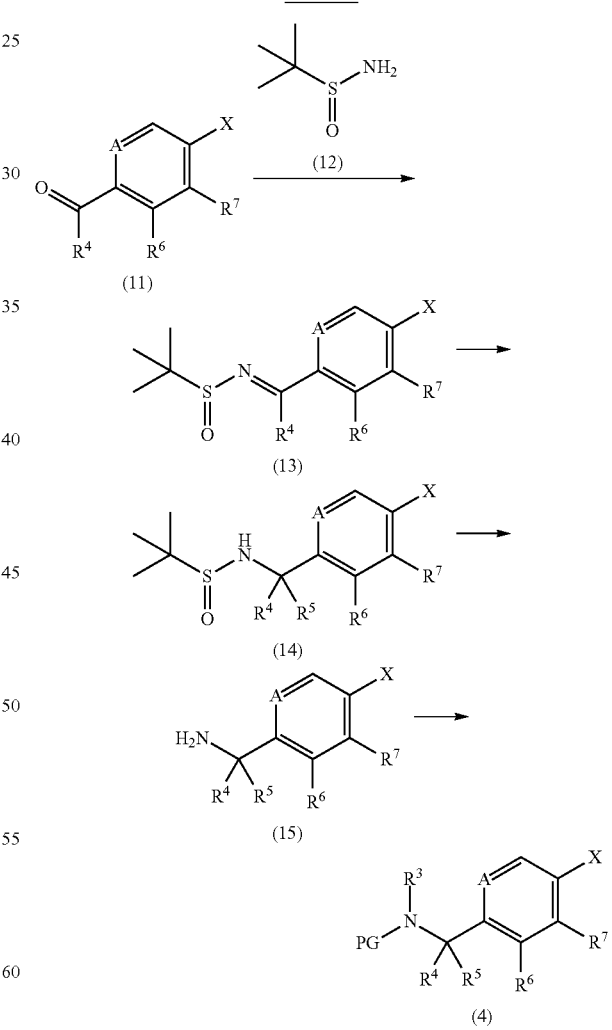

X is halogen, particularly, Br or I
PG is e.g. the Boc protecting group

Scheme 3 outlines the synthesis of Boc-protected primary amines of formula (4), wherein $R^3$ is hydrogen, PG is the Boc protecting group and X is halogen, particularly bromone or iodo. Carbonyl-compounds or formula (11) can be reacted either with (S)-2-methylpropane-2-sulfinamide, (R)-2-methylpropane-2-sulfinamide or racemic 2-methylpropane-2-sulfinamide (12) in presence of a catalytic amount of an acid such as pTsOH and an excess of a drying agent such as magnesium sulfate in a solvent such as DCM to obtain compounds of formula (13). Derivatives of formula (13) can be converted into sulfinamides of formula (14) by reaction with a Grignard reagent of general formula $R^5MgX$ (X=Cl, Br, I) or an organolithium reagent $R^5Li$. Compounds of formula (14) can be elaborated into derivatives of formula (4), wherein $R^3$ is hydrogen, PG is the Boc protecting group and X is halogen, particularly bromone or iodo, by acidic hydrolysis of the sulfonamide moiety using an acid such as HCl and subsequent introduction of the Boc protecting group into compounds of formula (15) with di-tert-butyl dicarbonate in presence of TEA. Primary amine derivatives of formula (15) can also be converted into secondary amines of formula (16) by N-alkylation with a reagent $R^3$—I or $R^3$—Br in presence of a base such as TEA. Introduction of a protecting group such as Boc into derivatives (16) delivers compounds of formula (4), wherein $R^3$ is alkyl or cycloalkyl (Scheme 4).

Scheme 4

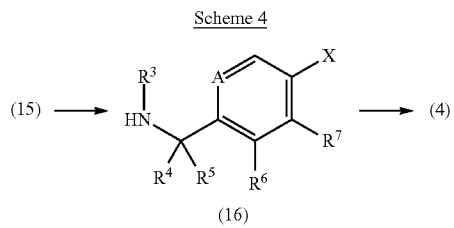

X is halogen, particularly, Br or I

Alternatively, amines of formula (4), wherein $R^4$ is hydrogen, PG is the acetyl protecting group and X is halogen, particularly bromone or iodo, may be prepared as illustrated in Scheme 5.

Scheme 5

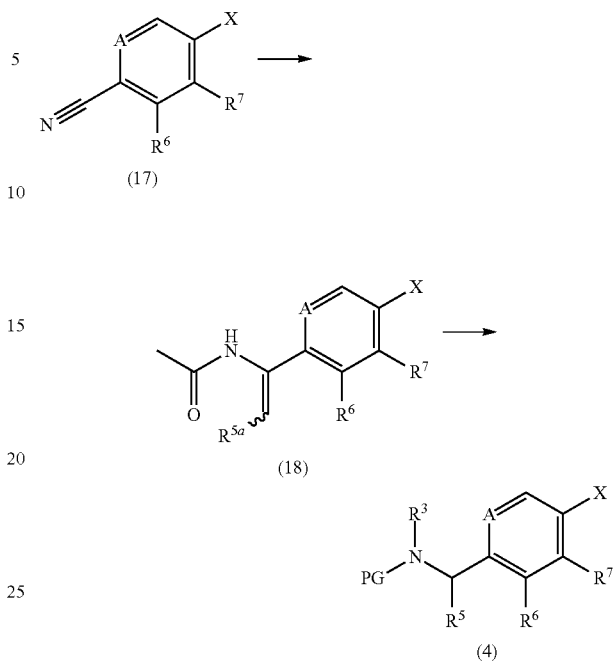

X is halogen, particularly, Br or I
PG is e.g. the Boc protecting group

Stepwise reaction of nitriles of formula (17) first with a Grignard reagent $R^5MgX$ (X is Cl, Br or I and $R^5$=CH$_2R^{5a}$) preferable at low temperature and second with acetic acid anhydride, delivers enamides of formula (18) which can be hydrogenated to derivatives of formula (4), wherein $R^3$ and $R^4$ are hydrogen and PG is the acetyl protecting group. If desired, this hydrogenation reaction can be performed in an enantioselective fashion, using catalysts composed of rhodium and chiral phosphine ligands such as combinations of Rh(COD)$_2$[BF$_4$] and Tangphos, DiPAMP or EtDuphos.

Another way to assemble amine derivatives of formula (2) is outlined in scheme 6.

Scheme 6

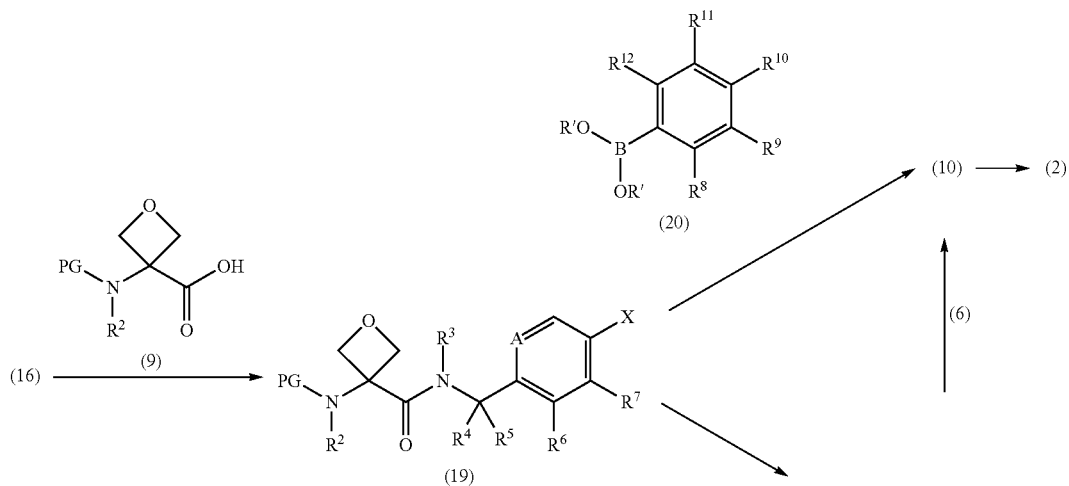

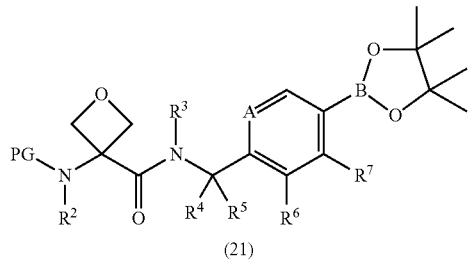

(21)

X is halogen, particularly, Br or I
PG is e.g. the Boc or the Fmoc protecting group Reaction of derivatives of formula (16) with suitable protected amino-oxetane-carboxylic acid derivatives of formula (9), wherein PG is a protecting group, employing coupling reagents such as EDCI/HOBT, HATU, TBTU, BOP-Cl, BOP, PyBop, DIC/HOBT or DCC/HOBT optionally in presence of a base such as TEA or DIPEA delivers amides of formula (19). Similarly, amides of formula (19), wherein $R^3$ is H can be obtained by reaction of compounds of formula (15) with compounds of formula (9). Compounds of formula (19) can be converted into compounds of formula (10) by reaction with arylboronic acid or arylboronic acid ester derivatives of formula (20), wherein R' is hydrogen or alkyl, using Suzuki reaction conditions, employing palladium catalysts such as [1,1'-bis(diphenylphosphino)ferrocene]palladium(II) chloride (1:1 complex with DCM), palladium(II) acetate in presence of tri-o-tolyl-phosphine or tetrakis(triphenylphosphine)palladium(0) and a base such as potassium carbonate. Alternatively, compounds of formula (19) can be converted into the boron ester derivatives of formula (21) using bis(pinacolato)diboron in presence of a palladium catalyst and potassium acetate in a polar, aprotic solvent such as DMF or DMSO. These boron ester derivatives of formula (21) can be elaborated into derivatives formula (10) by reaction with arylhalides of formula (6) using Suzuki reaction conditions as described above. Conversion of derivatives of formula (10) into amines of formula (2) can be accomplished as discussed for scheme (2).

Compounds of formula (I) may also be prepared as illustrated in scheme 7.

Scheme 7

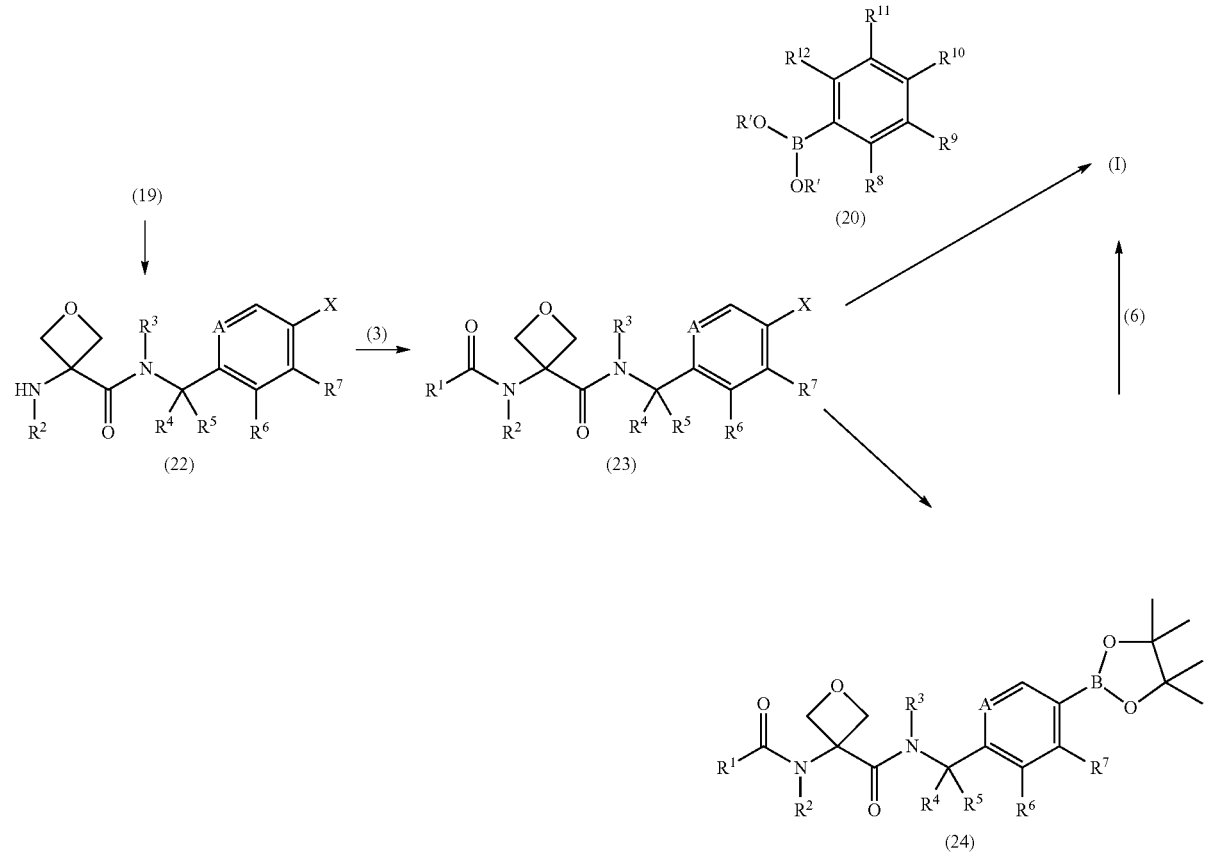

X is halogen, particularly, Br or I

Amine derivatives of formula (22) can be obtained from compounds of formula (19) by removal of the nitrogen protecting group using standard methods well known to those skilled in the art and described above for scheme 2. Reaction of amines of formula (22) with acid derivatives of formula (3) delivers compounds of formula (23). The appropriate reaction conditions depending on the nature of the acid derivative are described above for scheme 1. Reaction conditions for the elaboration of compounds of formula (23) into formula (I) compounds, either directly by reaction with boronic acid derivatives of formula (20) or stepwise via boron ester derivatives of formula (24) and subsequent reaction with arylhalides of formula (6), are discussed above for scheme 6.

Also an embodiment of the present invention is a process to prepare a compound of formula (I) as defined above comprising the reaction of a compound of formula (II) in the presence of a compound of formula (III);

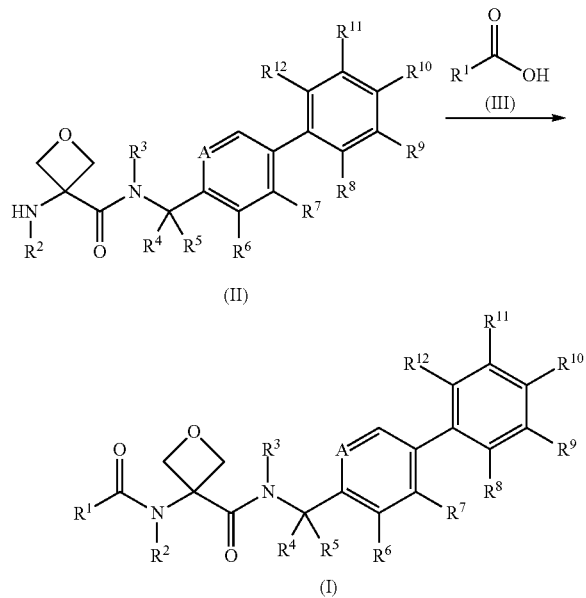

In particular in the presence of a coupling agent, particularly EDCI and HOBT, in the presence or not of a base, particularly in the presence of triethylamine, in a solvent, particularly DMF, at a temperature comprised between RT and reflux, wherein A, $R^1$, $R^2$, $R^3$, $R^4$, $R^5$, $R^6$, $R^7$, $R^8$, $R^9$, $R^{10}$ and $R^{12}$ are as defined herein.

Particular intermediates are selected from
4'-((R)-1-tert-Butoxycarbonylamino-ethyl)-3-chloro-3'-fluoro-biphenyl-2-carboxylic acid methyl ester;
{(R)-1-[3',5'-Dichloro-2'-(2,2-difluoro-ethoxy)-3-fluoro-biphenyl-4-yl]-ethyl}-carbamic acid tert-butyl ester;
{(R)-1-[5'-Chloro-3,3'-difluoro-2'-(5-methyl-[1,2,4]oxadiazol-3-yl)-biphenyl-4-yl]-ethyl}-carbamic acid tert-butyl ester;
{(R)-1-[5'-Chloro-3,3'-difluoro-2'-(2-methyl-2H-tetrazol-5-yl)-biphenyl-4-yl]-ethyl}-carbamic acid tert-butyl ester;
N—((R)-1-{5-[3,5-Dichloro-2-(2,2-difluoro-ethoxy)-phenyl]-3-fluoro-pyridin-2-yl}-ethyl)-acetamide;
N—((R)-1-{5-[5-Chloro-3-fluoro-2-(5-methyl-[1,2,4]oxadiazol-3-yl)-phenyl]-3-fluoro-pyridin-2-yl}-ethyl)-acetamide;
N—((R)-1-{5-[5-Chloro-3-fluoro-2-(2-methyl-2H-tetrazol-5-yl)-phenyl]-3-fluoro-pyridin-2-yl}-ethyl)-acetamide;
4'-((R)-1-Amino-ethyl)-3-chloro-3'-fluoro-biphenyl-2-carboxylic acid methyl ester;
(R)-1-[3',5'-Dichloro-2'-(2,2-difluoro-ethoxy)-3-fluoro-biphenyl-4-yl]-ethylamine;
(R)-1-[5'-Chloro-3,3'-difluoro-2'-(5-methyl-[1,2,4]oxadiazol-3-yl)-biphenyl-4-yl]-ethylamine;
(R)-1-[5'-Chloro-3,3'-difluoro-2'-(2-methyl-2H-tetrazol-5-yl)-biphenyl-4-yl]-ethylamine;
(R)-1-{5-[3,5-Dichloro-2-(2,2-difluoro-ethoxy)-phenyl]-3-fluoro-pyridin-2-yl}-ethylamine;
(R)-1-{5-[5-Chloro-3-fluoro-2-(5-methyl-[1,2,4]oxadiazol-3-yl)-phenyl]-3-fluoro-pyridin-2-yl}-ethylamine;
(R)-1-{5-[5-Chloro-3-fluoro-2-(2-methyl-2H-tetrazol-5-yl)-phenyl]-3-fluoro-pyridin-2-yl}-ethylamine;
3-Chloro-4'-((R)-1-{[3-(9H-fluoren-9-ylmethoxycarbonylamino)-oxetane-3-carbonyl]-amino}-ethyl)-3'-fluoro-biphenyl-2-carboxylic acid methyl ester;
(3-{(R)-1-[3',5'-Dichloro-2'-(2,2-difluoro-ethoxy)-3-fluoro-biphenyl-4-yl]-ethylcarbamoyl}-oxetan-3-yl)-carbamic acid 9H-fluoren-9-ylmethyl ester;
(3-{(R)-1-[5'-Chloro-3,3'-difluoro-2'-(5-methyl-[1,2,4]oxadiazol-3-yl)-biphenyl-4-yl]-ethylcarbamoyl}-oxetan-3-yl)-carbamic acid 9H-fluoren-9-ylmethyl ester;
(3-{(R)-1-[5'-Chloro-3,3'-difluoro-2'-(2-methyl-2H-tetrazol-5-yl)-biphenyl-4-yl]-ethylcarbamoyl}-oxetan-3-yl)-carbamic acid 9H-fluoren-9-ylmethyl ester;
[3-((R)-1-{5-[3,5-Dichloro-2-(2,2-difluoro-ethoxy)-phenyl]-3-fluoro-pyridin-2-yl}-ethylcarbamoyl)-oxetan-3-yl]-carbamic acid 9H-fluoren-9-ylmethyl ester; and
[3-((R)-1-{5-[5-Chloro-3-fluoro-2-(5-methyl-[1,2,4]oxadiazol-3-yl)-phenyl]-3-fluoro-pyridin-2-yl}-ethylcarbamoyl)-oxetan-3-yl]-carbamic acid 9H-fluoren-9-ylmethyl ester.

A further object of the present invention comprises a compound according to formula (I) as described herein, when manufactured according to any one of the described processes.

Also an object of the present invention is a compound according to formula (I) as described herein for use as therapeutically active substance.

Likewise an object of the present invention is a pharmaceutical composition comprising a compound according to formula (I) as described herein, or a pharmaceutically acceptable salt or ester thereof, and a therapeutically inert carrier.

Also an object of the present invention is the use of a compound according to formula (I) as described herein for the treatment or prophylaxis of illnesses which are caused by disorders mediated through the stimulation of bradykinin receptor pathway.

The present invention also relates to the use of a compound according to formula (I) as described herein for the treatment or prophylaxis of glomerulonephritides, Henoch-Schönlein purpura nephropathy, ANCA-associated crescentic glomerulonephritis, lupus nephritis and IgA nephritis.

Also an embodiment of the present invention is the use of a compound according to formula (I) as described herein for the treatment or prophylaxis of glomerulonephritides.

The present invention also relates to the use of a compound according to formula (I) as described herein for the preparation of a medicament for the treatment or prophylaxis of glomerulonephritides, Henoch-Schönlein purpura nephropathy, ANCA-associated crescentic glomerulonephritis, lupus nephritis and IgA nephritis.

Also an embodiment of the present invention is the use of a compound according to formula (I) as described herein for the preparation of a medicament for the treatment or prophylaxis of glomerulonephritides.

A particular embodiment of the present invention is a compound according to formula (I) as described herein for the treatment or prophylaxis of glomerulonephritides, Henoch-Schönlein purpura nephropathy, ANCA-associated crescentic glomerulonephritis, lupus nephritis and IgA nephritis.

Also a particular embodiment of the present invention is a compound according to formula (I) as described herein for the treatment or prophylaxis of glomerulonephritides.

Also an object of the invention is a method for the treatment or prophylaxis of glomerulonephritides, Henoch-Schönlein purpura nephropathy, ANCA-associated crescentic glomerulonephritis, lupus nephritis and IgA nephritis, which method comprises administering an effective amount of a compound according to formula (I) as described herein.

Also an embodiment of the present invention is a method for the treatment or prophylaxis of glomerulonephritides, which method comprises administering an effective amount of a compound according to formula (I) as described herein.

Assay Procedures

Receptor Binding Assay
Binding assays were done with membranes from CHO-K1 cells overexpressing Bradykinin-1 receptor.

For binding, Bradykinin-1 receptor antagonist compounds were added in various concentrations in 50 mM Tris pH 7.4, 5 mM $MgCl_2$ together with 6 nM Kallidin (Des $Arg^{10}$, $Leu^9$), [3,4-Prolyl-3,4-$^3$H(N)] (PerkinElmer, 1.85-4.44 TBq/mmol) to 40 µg membrane protein containing approximately 1 fmol Bradykinin-1 receptor and incubated for 15 min at 27° C. To determine non-specific binding 10 µM Lys-(Des-$Arg^9$)-Bradykinin (Bachem) was added. Membranes were harvested through GF/B (glass fiber filter; PerkinElmer) plates, equilibrated with 0.5% polyethylenimine, air dried at 50° C. for 2 hr. Radioactivity was determined by counting in a topcounter (NXT Packard). Specific binding was defined as total binding minus nonspecific binding and typically represents about 90-95% of the total binding. Antagonist activity is expressed as Ki: inhibitor concentration required for 50% inhibition of specific binding corrected for the concentration of the radioligand.

Calcium Mobilization Assay
GeneBLAzer® Bradykinin (B1)-NFAT-bla CHO-K1 cells (from Invitrogen) stably overexpressing the human bradykinin 1 receptor were cultured in DMEM (high glucose) supplemented with 10% dialysed FBS, 1% NEAA (non essential amino acids) 1% penicillin/streptomycin, 1% G418 and 0.1 mg/ml zeocin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

| Example | B1R Binding Ki [µM] | Ca mobilization IC50 [µM] |
| --- | --- | --- |
| 1 | 0.0026 | 0.0003 |
| 2 | 0.0119 | 0.0012 |
| 3 | 0.0024 | 0.0004 |
| 4 | 0.0025 | 0.0002 |
| 5 | 0.0011 | 0.0001 |
| 6 | 0.0065 | 0.0022 |
| 7 | 0.0016 | 0.0001 |
| 8 | 0.0053 | 0.0004 |
| 9 | 0.0051 | 0.0011 |
| 10 | 0.0047 | 0.0033 |
| 11 | 0.0026 | 0.0008 |
| 12 | 0.0008 | 0.0001 |
| 13 | 0.001 | 0.00004 |
| 14 | 0.0014 | 0.0002 |
| 15 | 0.0011 | 0.0001 |
| 16 | 0.0016 | 0.0004 |
| 17 | 0.025 | 0.0266 |
| 18 | 0.003 | 0.0011 |
| 19 | 0.0051 | 0.0012 |
| 20 | 0.0016 | 0.0004 |
| 21 | 0.0043 | 0.001 |
| 22 | 0.0017 | 0.0005 |
| 23 | 0.001 | 0.0001 |
| 24 | 0.0012 | 0.0001 |
| 25 | 0.001 | 0.0004 |
| 26 | 0.503 | 0.4902 |
| 27 | 0.0826 | 0.1074 |
| 28 | 0.0014 | 0.0001 |
| 29 | 0.0141 | 0.0094 |
| 30 | 0.0013 | 0.0002 |
| 31 | 0.0006 | <0.000032 |
| 32 | 0.0023 | 0.0002 |
| 33 | 0.0199 | 0.0053 |
| 34 | 0.0022 | 0.0004 |
| 35 | 0.0033 | 0.0003 |
| 36 | 0.0012 | 0.0002 |
| 37 | 0.0035 | 0.0004 |
| 38 | 0.0043 | 0.0006 |
| 39 | 0.0087 | 0.0039 |
| 40 | 0.0011 | 0.0001 |
| 41 | 0.0071 | 0.0036 |
| 42 | 0.119 | 0.2009 |
| 43 | 0.0014 | 0.0001 |
| 44 | 0.0011 | 0.0001 |

Compounds of formula (I) and their pharmaceutically acceptable salts or esters thereof as described herein have $IC_{50}$ values between 0.000001 uM and 1000 uM, particular compounds have $IC_{50}$ values between 0.000005 uM and 500 uM, further particular compounds have $IC_{50}$ values between 0.00005 uM and 5 uM. Compounds of formula (I) and their pharmaceutically acceptable salts or esters thereof as described herein have Ki values between 0.0000001 uM and 1000 uM, particular compounds have $IC_{50}$ values between 0.0000005 uM and 500 uM, further particular compounds have $IC_{50}$ values between 0.000005 uM and 50 uM. These results have been obtained by using the foregoing binding and/or calcium mobilization assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of pain including, for example, visceral pain (such as pancreatitis, interstitial cystitis, renal colic, prostatitis, chronic pelvic pain), neuropathic pain (such as post-herpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (e.g., post-mastectomy syndrome, post-thoracotomy syndrome, stump pain), bone and joint pain (osteoarthritis), spine pain (e.g., acute and chronic low back pain, neck pain, spinal stenosis), shoulder pain, repetitive motion pain, dental pain, sore throat, cancer pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (e.g. osteoarthritis, rheumatoid arthritis, rheumatic disease, teno-synovitis and gout, ankylosing spondylitis, bursitis).

Furthermore, the compounds of formula (I) or their pharmaceutically acceptable salts and esters as described herein can also be used to treat hyperreactive airways and to treat inflammatory events associated with airways disease (e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome").

The compounds of formula (I) or their pharmaceutically acceptable salts and esters as described herein may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssnoss.

In another embodiment, the compounds of formula (I) or their pharmaceutically acceptable salts and esters as described herein may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema, brain inflammation, stroke and angioedema.

The compounds of formula (I) or their pharmaceutically acceptable salts and esters as described herein may also be used for the treatment of glomerulonephritides and other inflammatory kidney diseases, including Henoch-Schönlein purpura nephropathy (HSPN) and ANCA-associated crescentic glomerulonephritis. They may be used to treat obesity, diabetes, diabetic vasculopathy, diabetic neuropathy, diabetic retinopathy, post-capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, e.g., Parkinson's and Alzheimers disease, epilepsy, septic shock, e.g. as anti-hypovolemic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Intermediate 1

3-Amino-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide

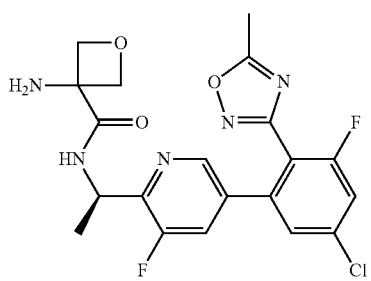 [SMILES: Cc1nc(-c2c(F)cc(Cl)cc2-c2cnc([C@@H](C)NC(=O)C3(N)COC3)c(F)c2)no1]

Step A: N—((R)-1-{5-[5-Chloro-3-fluoro-2-(5-methyl-[1,2,4]oxadiazol-3-yl)-phenyl]-3-fluoro-pyridin-2-yl}-ethyl)-acetamide

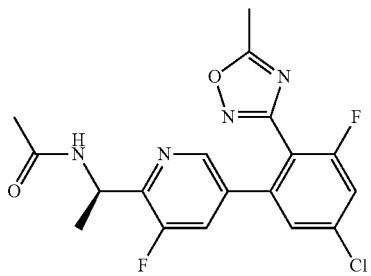 [SMILES: CC(=O)N[C@H](C)c1ncc(-c2cc(Cl)cc(F)c2-c2noc(C)n2)cc1F]

A stream of argon was bubbled through a mixture of N—[(R)-1-(5-bromo-3-fluoro-pyridin-2-yl)-ethyl]-acetamide (200 mg, 0.766 mmol, intermediate 12) potassium acetate (226 mg, 2.3 mmol) and bis(pinacolato)diboron (253 mg, 0.996 mmol) in DMSO (1.5 ml) in a sealed tube for 10 min. Then [1,1'-bis(diphenylphosphino)ferrocene]palladium (II) chloride 1:1 complex with DCM (31.3 mg, 0.0383 mmol) was added and again a stream of argon was bubbled through the reaction mixture for 10 min. The tube was then sealed and heated to 90° C. for 1.5 h. After cooling to room temperature, potassium carbonate (212 mg, 1.53 mmol), water (198 μl), 3-(2-bromo-4-chloro-6-fluoro-phenyl)-5-methyl-[1,2,4]oxadiazole (246 mg, 0.843 mmol, intermediate 10) and additional [1,1'-bis(diphenylphosphino)ferrocene]palladium(II) chloride 1:1 complex with DCM (31.3 mg, 0.0383 mmol) were added and the reaction mixture was heated to 80° C. for 3 h. The mixture was cooled to room temperature, diluted with water and extracted three times with EtOAc. The combined organic layers were washed two times with water and brine, dried with Na$_2$SO$_4$ and evaporated. The remaining brown gum was purified by chromatography (silica gel; heptane/EtOAc 35:65-10:90) and the title compound was obtained as off white foam (200 mg, 66%). MS: 393.1 [M+H]$^+$.

Step B: (R)-1-{5-[5-Chloro-3-fluoro-2-(5-methyl-[1,2,4]oxadiazol-3-yl)-phenyl]-3-fluoro-pyridin-2-yl}-ethylamine

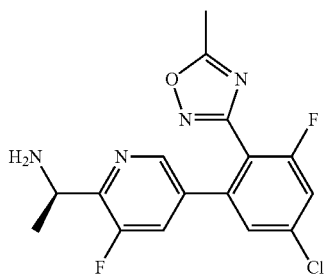 [SMILES: Cc1nc(-c2c(F)cc(Cl)cc2-c2cnc([C@@H](C)N)c(F)c2)no1]

A suspension of N—((R)-1-{5-[5-chloro-3-fluoro-2-(5-methyl-[1,2,4]oxadiazol-3-yl)-phenyl]-3-fluoro-pyridin-2-yl}-ethyl)-acetamide (195 mg, 0.496 mmol, step A) in 2N HCl (2.5 ml, 5.00 mmol) was heated to 75° C. overnight. The colorless solution was cooled to room temperature, diluted with water and the pH was adjusted to 12 by addition of 1N NaOH. The mixture was then extracted three times with EtOAc and the combined organic layers were washed with brine (pH adjusted to 12 with 1N NaOH), dried with Na$_2$SO$_4$ and evaporated. The crude title compound (167 mg, 96%, light yellow gum) was used in the next reaction step without further purification. MS: 351.1 [M+H]$^+$.

Step C: [3-((R)-1-{5-[5-Chloro-3-fluoro-2-(5-methyl-[1,2,4]oxadiazol-3-yl)-phenyl]-3-fluoro-pyridin-2-yl}-ethylcarbamoyl)-oxetan-3-yl]-carbamic acid 9H-fluoren-9-ylmethyl ester

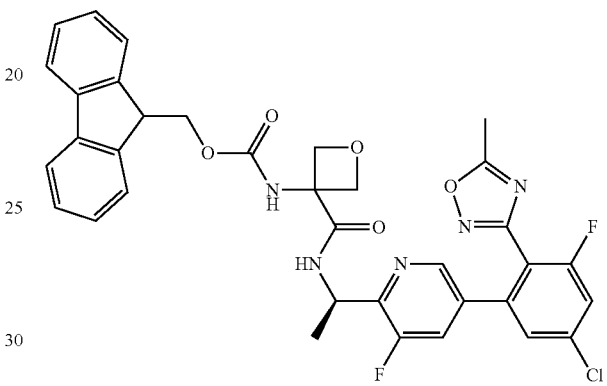

To a solution of 3-(9H-fluoren-9-ylmethoxycarbonylamino)-oxetane-3-carboxylic acid (77.4 mg, 0.228 mmol, intermediate 8) in dry DMF (2 ml) were added N-(3-dimethylaminopropyl)-N'-ethylcarbodiimide hydrochloride (48.1 mg, 0.251 mmol) and 1-hydroxybenzotriazole hydrate (38.4 mg, 0.251 mmol) at room temperature. The resulting colorless solution was stirred for 5 min before a solution of (R)-1-{5-[5-chloro-3-fluoro-2-(5-methyl-[1,2,4]oxadiazol-3-yl)-phenyl]-3-fluoro-pyridin-2-yl}-ethylamine (80.0 mg, 0.228 mmol, step B) in dry DMF (2 ml) was added. This mixture was stirred at room temperature for 1.5 h. Then water was added, the pH was adjusted to 7 with sat. NaHCO$_3$ solution and the mixture was extracted three times with EtOAc. The combined organic layers were washed three times with water and then with brine, dried with Na$_2$SO$_4$ and evaporated. The remaining light brown foam was purified by chromatography (silica gel; DCM/MeOH 98:2-95:5) and the title compound was obtained as off white foam (150 mg, 98%). MS: 672.3 [M+H]$^+$.

Step D: 3-Amino-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide To a solution of [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-carbamic acid 9H-fluoren-9-ylmethyl ester (71.9 mg, 0.107 mmol, step C) in DCM (5 ml) was added piperidine (0.5 ml) and the mixture was stirred at room temperature for 1 h. The colorless solution was concentrated to dryness under high vacuum. The remaining residue was purified by chromatography (silica gel; DCM/MeOH 98:2-95:5) and the title compound was obtained as colorless gum (36 mg, 75%). MS: 450.2 [M+H]⁺.

Intermediate 2

3-Amino-oxetane-3-carboxylic acid ((R)-1-{5-[3,5-dichloro-2-(2,2-difluoro-ethoxy)-phenyl]-3-fluoro-pyridin-2-yl}-ethyl)-amide

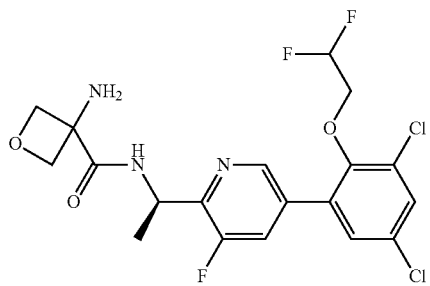 [SMILES: C[C@@H](NC(=O)C1(N)COC1)c1ncc(-c2cc(Cl)cc(Cl)c2OCC(F)F)cc1F]

The title compound was prepared in analogy to intermediate 1 synthesizing N—((R)-1-{5-[3,5-dichloro-2-(2,2-difluoro-ethoxy)-phenyl]-3-fluoro-pyridin-2-yl}-ethyl)-acetamide in step A (using 1-bromo-3,5-dichloro-2-(2,2-difluoro-ethoxy)-benzene (intermediate 9) instead of 3-(2-bromo-4-chloro-6-fluoro-phenyl)-5-methyl-[1,2,4]oxadiazole), (R)-1-{5-[3,5-dichloro-2-(2,2-difluoro-ethoxy)-phenyl]-3-fluoro-pyridin-2-yl}-ethylamine in step B and [3-((R)-1-{5-[3,5-dichloro-2-(2,2-difluoro-ethoxy)-phenyl]-3-fluoro-pyridin-2-yl}-ethylcarbamoyl)-oxetan-3-yl]-carbamic acid 9H-fluoren-9-ylmethyl ester in step C. White foam. MS: 464.1 [M+H]⁺.

Intermediate 3

3-Amino-oxetane-3-carboxylic acid ((R)-1-{5-[5-chloro-3-fluoro-2-(2-methyl-2H-tetrazol-5-yl)-phenyl]-3-fluoro-pyridin-2-yl}-ethyl)-amide

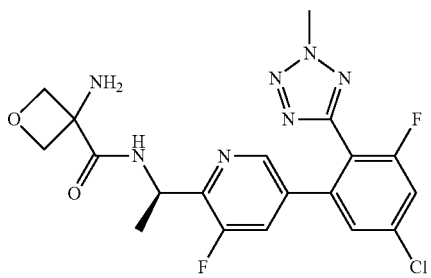 [SMILES: C[C@@H](NC(=O)C1(N)COC1)c1ncc(-c2cc(Cl)cc(F)c2-c2nnn(C)n2)cc1F]

The title compound was prepared in analogy to intermediate 1 synthesizing N—((R)-1-{5-[5-chloro-3-fluoro-2-(2-methyl-2H-tetrazol-5-yl)-phenyl]-3-fluoro-pyridin-2-yl}-ethyl)-acetamide in step A (using 5-(2-bromo-4-chloro-6-fluoro-phenyl)-2-methyl-2H-tetrazole (intermediate 11) instead of 3-(2-bromo-4-chloro-6-fluoro-phenyl)-5-methyl-[1,2,4]oxadiazole), (R)-1-{5-[5-chloro-3-fluoro-2-(2-methyl-2H-tetrazol-5-yl)-phenyl]-3-fluoro-pyridin-2-yl}-ethylamine in step B and [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-carbamic acid 9H-fluoren-9-ylmethyl ester in step C. White solid. MS: 450.2 [M+H]⁺.

Intermediate 4

4'-{(R)-1-[(3-Amino-oxetane-3-carbonyl)-amino]-ethyl}-3-chloro-3'-fluoro-biphenyl-2-carboxylic acid methyl ester

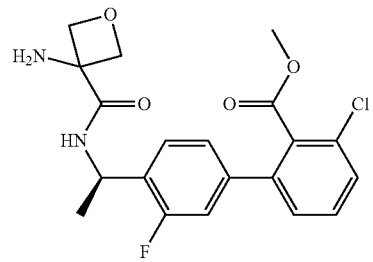 [SMILES: COC(=O)c1c(Cl)cccc1-c1ccc([C@@H](C)NC(=O)C2(N)COC2)c(F)c1]

Step A: 4'-((R)-1-tert-Butoxycarbonylamino-ethyl)-3-chloro-3'-fluoro-biphenyl-2-carboxylic acid methyl ester

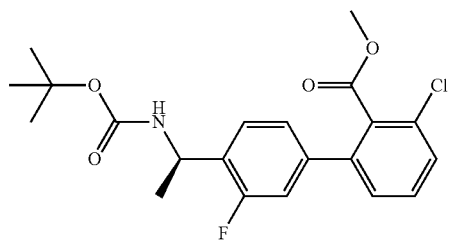 [SMILES: COC(=O)c1c(Cl)cccc1-c1ccc([C@@H](C)NC(=O)OC(C)(C)C)c(F)c1]

A mixture of {(R)-1-[2-fluoro-4-(4,4,5,5-tetramethyl-[1,3,2]dioxaborolan-2-yl)-phenyl]-ethyl}-carbamic acid tert-butyl ester (600 mg, 1.64 mmol, intermediate 13), methyl 2-bromo-6-chlorobenzoate (430 mg, 1.72 mmol) [CAS 685892-23-3; commercially available], tri-o-tolyl-phosphane (100 mg, 329 μmol), potassium carbonate (568 mg, 4.11 mmol) and palladium(II) acetate (18.4 mg, 82.1 μmol) in THF (20.0 ml) and water (1.18 ml) was stirred at room temperature over night. The reaction mixture was diluted with water and extracted three times with EtOAc. The combined extracts were washed with water and brine, dried with Na₂SO₄ and concentrated in vacuo. The remaining residue was purified by chromatography (silica gel; DCM/EtOAc 100:0-90:10) and the title compound was obtained as colorless oil (385 mg, 58%). MS: 466.1 [M−H+OAc]⁻.

Step B: 4'-((R)-1-Amino-ethyl)-3-chloro-3'-fluoro-biphenyl-2-carboxylic acid methyl ester hydrochloride

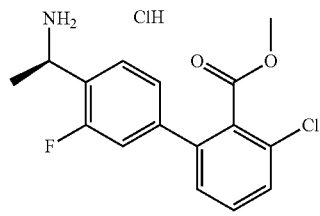 [SMILES: Cl ; COC(=O)c1c(Cl)cccc1-c1ccc([C@@H](C)N)c(F)c1]

4'-((R)-1-tert-Butoxycarbonylamino-ethyl)-3-chloro-3'-fluoro-biphenyl-2-carboxylic acid methyl ester (350 mg, 858 µmol, step A) was added to a solution of HCl in dioxane (4N, 4.29 ml, 17.2 mmol) and the reaction mixture was stirred at room temperature for 2 h. The reaction mixture was evaporated to dryness and the remaining solid was triturated with heptane/EtOAc 2:1 for 4 h. Filtration delivered the title compound as white solid (217 mg, 74%). MS: 308.2 [M+H]$^+$.

Step C: 3-Chloro-4'-((R)-1-{[3-(9H-fluoren-9-yl-methoxycarbonylamino)-oxetane-3-carbonyl]-amino}-ethyl)-3'-fluoro-biphenyl-2-carboxylic acid methyl ester

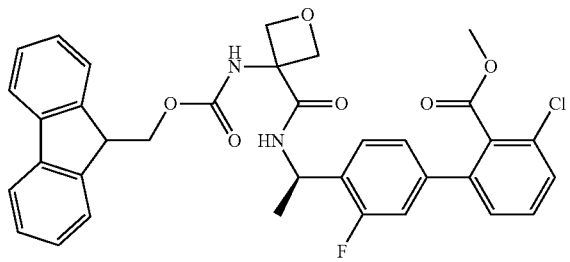 [SMILES: COC(=O)c1c(Cl)cccc1-c1ccc([C@@H](C)NC(=O)C2(NC(=O)OCC3c4ccccc4-c4ccccc43)COC2)c(F)c1]

To a solution of 3-(9H-fluoren-9-ylmethoxycarbonylamino)-oxetane-3-carboxylic acid (207 mg, 610 µmol, intermediate 8) in dry DMF (2.11 ml) were added N-(3-dimethylaminopropyl)-N'-ethylcarbodiimide hydrochloride (129 mg, 671 µmol) and 1-hydroxybenzotriazole hydrate (103 mg, 671 µmol) at room temperature. The colorless solution was stirred for 10 min before a solution of 4'-((R)-1-amino-ethyl)-3-chloro-3'-fluoro-biphenyl-2-carboxylic acid methyl ester hydrochloride (210 mg, 610 µmol) and triethylamine (61.7 mg, 85.0 µl, 610 µmol) in dry DMF (2.11 ml) was added. After addition, the brown solution was stirred at room temperature over night. Then water was added and the pH of the mixture was adjusted to 7 by addition of sat. NaHCO$_3$ solution. The mixture was extracted three times with EtOAc and the combined organic layers were washed with water and brine, dried with Na$_2$SO$_4$ and evaporated. The remaining residue was purified by chromatography (silica gel; DCM/MeOH 99:1-95:5) and the title compound was obtained as white solid (312 mg, 81%). MS: 629.3 [M+H]$^+$.

Step D: 4'-{(R)-1-[(3-Amino-oxetane-3-carbonyl)-amino]-ethyl}-3-chloro-3'-fluoro-biphenyl-2-carboxylic acid methyl ester To a solution of 3-chloro-4'-((R)-1-{[3-(9H-fluoren-9-ylmethoxycarbonylamino)-oxetane-3-carbonyl]-amino}-ethyl)-3'-fluoro-biphenyl-2-carboxylic acid methyl ester (100 mg, 159 µmol, step C) in dry DMF (1.8 ml) was added piperidine (0.2 ml) and the solution was stirred at room temperature for 2 h. The brown solution was concentrated to dryness under high vacuum. The remaining residue was purified by chromatography (silica gel; DCM/MeOH 98:2) and the title compound was obtained as white solid (60 mg, 92%). MS: 407.2 [M+H]$^+$.

Intermediate 5

3-Amino-oxetane-3-carboxylic acid {(R)-1-[5'-chloro-3,3'-difluoro-2'-(2-methyl-2H-tetrazol-5-yl)-biphenyl-4-yl]-ethyl}-amide

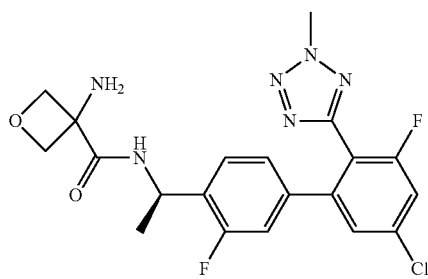 [SMILES: C[C@@H](NC(=O)C1(N)COC1)c1ccc(-c2cc(Cl)cc(F)c2-c2nnn(C)n2)cc1F]

The title compound was prepared in analogy to intermediate 4 using a modified procedure in step A for the synthesis of {(R)-1-[5'-chloro-3,3'-difluoro-2'-(2-methyl-2H-tetrazol-5-yl)-biphenyl-4-yl]-ethyl}-carbamic acid tert-butyl ester:

A mixture of {(R)-1-[2-fluoro-4-(4,4,5,5-tetramethyl-[1,3,2]dioxaborolan-2-yl)-phenyl]-ethyl}-carbamic acid tert-butyl ester (600 mg, 1.64 mmol, intermediate 13), 5-(2-bromo-4-chloro-6-fluorophenyl)-2-methyl-2H-tetrazole (479 mg, 1.64 mmol, intermediate 11), bis(diphenylphosphino)ferrocene]palladium(II) chloride 1:1 complex with DCM (67.1 mg, 82.1 µmol) and potassium carbonate (613 mg, 4.44 mmol) in DMSO (12.00 ml) and water (1.2 mL) was heated to 80° C. for 4 h and then stirred at room temperature over night. Water was added and the mixture was extracted three times with EtOAc. The combined extracts were washed with brine, dried with Na$_2$SO$_4$ and concentrated. The remaining brown oil was purified by chromatography (silica gel; heptane/EtOAc 1:1-1:2) and the title compound was obtained as white solid (312 mg, 42%). MS: 450.2 [M+H]$^+$.

The preparation continued by synthesis of (R)-1-[5'-chloro-3,3'-difluoro-2'-(2-methyl-2H-tetrazol-5-yl)-biphenyl-4-yl]-ethylamine in step B and (3-{(R)-1-[5'-chloro-3,3'-difluoro-2'-(2-methyl-2H-tetrazol-5-yl)-biphenyl-4-yl]-ethylcarbamoyl}-oxetan-3-yl)-carbamic acid 9H-fluoren-9-ylmethyl ester in step C.

White solid. MS: 449.2 [M+H]$^+$.

Intermediate 6

3-Amino-oxetane-3-carboxylic acid {(R)-1-[5'-chloro-3,3'-difluoro-2'-(5-methyl-[1,2,4]oxadiazol-3-yl)-biphenyl-4-yl]-ethyl}-amide

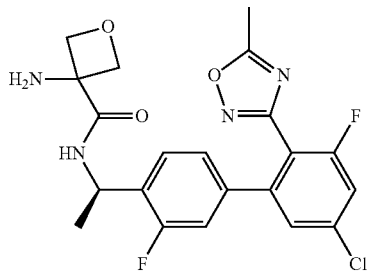 [SMILES: Cc1nc(-c2c(F)cc(Cl)cc2-c2ccc([C@@H](C)NC(=O)C3(N)COC3)c(F)c2)no1]

The title compound was prepared in analogy to intermediate 5 synthesizing {(R)-1-[5'-chloro-3,3'-difluoro-2'-(5-methyl-[1,2,4]oxadiazol-3-yl)-biphenyl-4-yl]ethyl}-carbamic acid tert-butyl ester in step A (using 3-(2-bromo-4-chloro-6-fluoro-phenyl)-5-methyl-[1,2,4]oxadiazole (intermediate 10) instead of 5-(2-bromo-4-chloro-6-fluorophenyl)-2-methyl-2H-tetrazole), (R)-1-[5'-chloro-3,3'-difluoro-2'-(5-methyl-[1,2,4]oxadiazol-3-yl)-biphenyl-4-yl]-ethylamine in step B and (3-{(R)-1-[5'-chloro-3,3'-difluoro-2'-(5-methyl-[1,2,4]oxadiazol-3-yl)-biphenyl-4-yl]-ethylcarbamoyl}-oxetan-3-yl)-carbamic acid 9H-fluoren-9-ylmethyl ester in step C. White foam. MS: 449.1; [M+H]+.

Intermediate 7

3-Amino-oxetane-3-carboxylic acid {(R)-1-[3',5'-dichloro-2'-(2,2-difluoro-ethoxy)-3-fluoro-biphenyl-4-yl]-ethyl}-amide

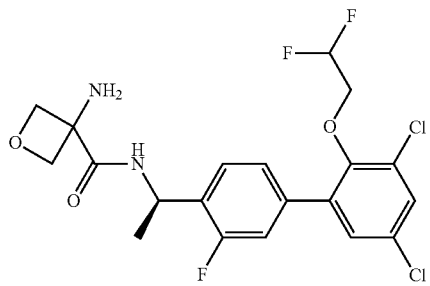 [SMILES: C[C@@H](NC(=O)C1(N)COC1)c1ccc(-c2cc(Cl)cc(Cl)c2OCC(F)F)cc1F]

The title compound was prepared in analogy to intermediate 4 synthesizing {(R)-1-[3',5'-dichloro-2'-(2,2-difluoro-ethoxy)-3-fluoro-biphenyl-4-yl]-ethyl}-carbamic acid tert-butyl ester in step A (using 1-bromo-3,5-dichloro-2-(2,2-difluoro-ethoxy)-benzene (intermediate 9) instead of methyl 2-bromo-6-chlorobenzoate), (R)-1-[3',5'-dichloro-2'-(2,2-difluoro-ethoxy)-3-fluoro-biphenyl-4-yl]-ethylamine in step B and (3-{(R)-1-[3',5'-dichloro-2'-(2,2-difluoro-ethoxy)-3-fluoro-biphenyl-4-yl]-ethylcarbamoyl}-oxetan-3-yl)-carbamic acid 9H-fluoren-9-ylmethyl ester in step C. Colorless oil. MS: 463.1; [M+H]+.

Intermediate 8

3-(9H-Fluoren-9-ylmethoxycarbonylamino)-oxetane-3-carboxylic acid

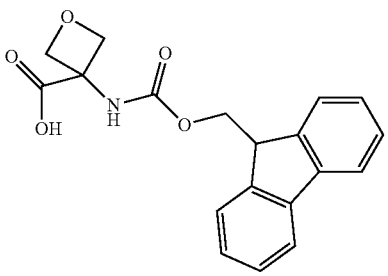 [SMILES: O=C(NC1(C(=O)O)COC1)OCC1c2ccccc2-c2ccccc21]

A solution of (9H-fluoren-9-yl)methyl 2,5-dioxopyrrolidin-1-yl carbonate (3.2 g, 9.5 mmol) in dioxane (30 ml) was added to a solution of 3-amino-oxetane-3-carboxylic acid (1.17 g, 10 mmol) [CAS 138650-24-5; Synlett 1991, 783-784] and potassium carbonate (2.76 g, 20.0 mmol) in water (30 ml). The light yellow opaque solution was stirred at room temperature for 75 minutes. During that time, a white solid precipitated. The mixture was diluted with water and extracted two times with diethyl ether. The white solid did not dissolve and was kept therefore in the aqueous layer, which was acidified to pH 2 by addition of 1N HCl and extracted three times with EtOAc. The combined EtOAc layers were washed with brine, dried with Na$_2$SO$_4$ and evaporated.

The crude title compound was obtained as white solid and was used without further purification.

Intermediate 9

1-Bromo-3,5-dichloro-2-(2,2-difluoro-ethoxy)-benzene

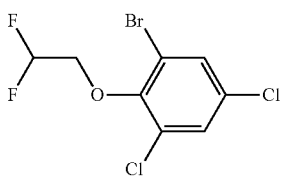 [SMILES: FC(F)COc1c(Cl)cc(Cl)cc1Br]

Step A: 2-Bromo-4,6-dichloro-phenol

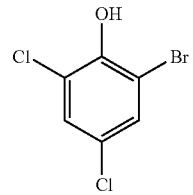

To a solution of 2,4-dichloro-phenol (15 g, 19.02 mmol) in toluene (200 ml) was added bromine (5.1 ml, 184.04 mmol) dropwise at −50° C. Then tert.-butylamine (19.4 ml, 99.02 mmol) was added dropwise and the reaction mixture was stirred at −50° C. for 30 minutes. The reaction was quenched by addition of 38% aqueous NaHSO$_3$ solution, the organic layer was separated and the aqueous layer was extracted two times with EtOAc. The combined organic extracts were dried with Na$_2$SO$_4$, filtered and evaporated to obtain the title compound as white solid (21.5 g, 96%).

Step B: Methanesulfonic acid 2,2-difluoro-ethyl ester

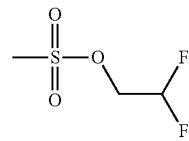

To a solution of 2,2-difluoro-ethanol (6 g, 73.12 mmol) and mesyl chloride (6.26 ml, 80.43 mmol)) in DCM (40 ml) was added triethylamine (12.66 ml, 87.74 mmol) dropwise at 0° C. After the addition was completed, the mixture was allowed to warm to room temperature and was stirred for 1 h. The reaction mixture was then washed two times with water and with brine and dried with Na$_2$SO$_4$. Evaporation of the solvent yielded the title compound as yellow liquid (10.7 g, 92%).

Step C: 1-Bromo-3,5-dichloro-2-(2,2-difluoro-ethoxy)-benzene

To a solution of 2-bromo-4,6-dichloro-phenol (14.6 g, 60.3 mmol, Step A compound) in DMF (10 ml) were added K$_2$CO$_3$ (16.53 g, 120.6 mmol) and methanesulfonic acid 2,2-difluoro-ethyl ester (10.7 g, 66.4 mmol, Step B compound) and the mixture was heated to reflux for 16 h. The DMF was then evaporated in vacuo and the resulting residue was dissolved in EtOAc (300 ml). This solution was washed two times with water, with brine, dried with Na$_2$SO$_4$ and evaporated. The remaining crude product was purified by chromatography (silica gel; hexane) and the title compound was obtained as white solid (14.5 g, 79%). MS: m/z=304 [M]$^+$.

Intermediate 10

3-(2-Bromo-4-chloro-6-fluoro-phenyl)-5-methyl-[1,2,4]oxadiazole

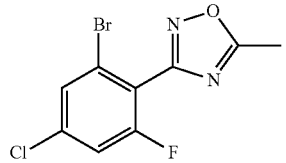

Step A: 2-Bromo-4-chloro-6-fluoro-benzaldehyde

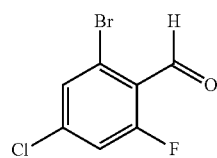

To a solution of 1,2-dibromo-5-chloro-3-fluoro-benzene (10 g, 34.68 mmol) in heptane (27 ml) was added THF (44 ml) and the mixture was cooled to −45° C. Then iPrMgCl (38.14 ml, 38.14 mmol, 1M solution in THF) was added dropwise to the reaction mixture maintaining the temperature between −40° C. to −45° C. The mixture was stirred for 30 minutes at −40° C. before DMF (13.4 ml, 173.4 mmol) was added dropwise to the reaction mixture maintaining the temperature between −45° C. to −20° C. After stirring for another 15 minutes at −20° C., the reaction mixture was poured into a mixture of 2N HCl (20 ml) and ether (50 ml) at 0° C. The organic layer was separated and the aqueous layer was extracted two times with ether. The combined organic layers were dried with Na$_2$SO$_4$ and evaporated in vacuo to obtain the title compound as yellow solid (7.8 g, 95%).

Step B: 2-Bromo-4-chloro-6-fluoro-benzaldehyde oxime

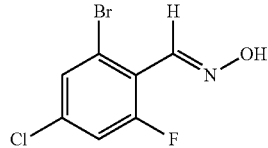 [SMILES: O/N=C/c1c(F)cc(Cl)cc1Br]

To a solution of 2-bromo-4-chloro-6-fluoro-benzaldehyde (15 g, 63.16 mmol) in 2-propanol (130 ml) was added hydroxyl amine hydrate (50% solution in water, 4.55 g, 68.90 mmol) at 25° C. and the mixture was warmed to 40° C. for 2 h. Water (55 ml) was then added slowly to this mixture and the slurry was aged for 1 h at 20° C. The reaction mixture was filtered and the remaining solid was washed with a mixture of 2-propanol and water (1.5:1) and dried under vacuum to yield the title compound as white solid (12.5 g, 77%).

Step C: 2-Bromo-4-chloro-6-fluoro-N-hydroxy-benzamidine

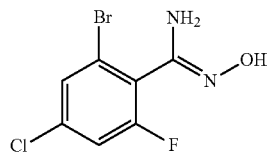 [SMILES: N/C(=N\O)c1c(F)cc(Cl)cc1Br]

A solution of N-chlorosuccinimide (8.34 g, 62.49 mmol) in DMF (25 ml) was added slowly to a solution of 2-bromo-4-chloro-6-fluoro-benzaldehyde oxime (15 g, 59.52 mmol) in DMF (50 ml) at 50° C. After completion of the addition, the reaction mixture was allowed to stir for 30 min at 50° C. The reaction mixture was then cooled to 3-5° C. and NH$_4$OH (4.6 ml, 119 mmol) was added dropwise. During addition the temperature was maintained between 0-10° C. and the reaction mixture was stirred for another 15 minutes at the same temperature. EtOAc and brine were then added and the mixture was agitated vigorously for 10 minutes before the phases were allowed to settle. The aqueous layer was separated and extracted two times with EtOAc. The combined organic layers were dried with Na$_2$SO$_4$ and evaporated to obtain the title compound as off white solid (13 g, 82%).

Step D: 3-(2-Bromo-4-chloro-6-fluoro-phenyl)-5-methyl-[1,2,4]oxadiazole

To a solution of 2-bromo-4-chloro-6-fluoro-N-hydroxy-benzamidine (26.5 g, 99.25 mmol) in 2-propanol (200 ml) was added N,N-dimethylacetamide dimethyl acetal (35.2 ml, 238.20 mmol) slowly at 25° C. and the reaction mixture was stirred for 30 minutes. After completion of the reaction all volatiles were evaporated and the resulting crude product was purified by chromatography (silica gel; hexane/EtOAc 97:3) to obtain the title compound as white solid (27.5 g, 58%). MS: m/z=290 [M]+.

Intermediate 11

5-(2-Bromo-4-chloro-6-fluoro-phenyl)-2-methyl-2H-tetrazole

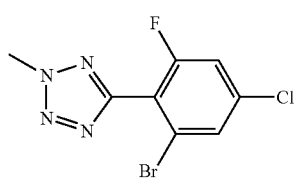

Step A: 2-Bromo-4-chloro-6-fluoro-benzonitrile

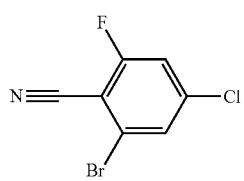 [SMILES: N#Cc1c(F)cc(Cl)cc1Br]

To a solution of 2-bromo-4-chloro-6-fluoro-phenylamine (10 g, 44.5 mmol) in anhydrous DCM (100 ml) was added nitrosonium tetrafluoroborate (5.72 g, 49.01 mmol) and the mixture was stirred at 25° C. for 1 h. The reaction mixture was then cooled to 0° C. prior to addition of KCN (5.8 g, 89.1 mmol) followed by a dropwise addition of an aqueous solution (50 ml) of cupric sulfate hexahydrate (22.24 g, 89.1 mmol). After stirring for 40 minutes at 0° C. the reaction mixture was allowed to warm to 25° C. and stirring was continued for 1 h. The reaction mixture was diluted with DCM (100 ml) and slowly quenched by the addition of aqueous saturated solution of NaHCO$_3$ until gas evolution is no longer observed. The resulting heterogeneous mixture was then filtered through a pad of celite and the organic layer was separated, washed twice with brine, dried with Na$_2$SO$_4$ and evaporated. The crude residue thus obtained was purified by chromatography (silica gel; hexane/EtOAc 90:10) to obtain the title compound as reddish solid (4 g, 38%).

Step B: 5-(2-Bromo-4-chloro-6-fluoro-phenyl)-2H-tetrazole

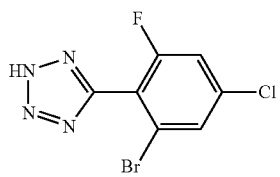 [SMILES: Fc1cc(Cl)cc(Br)c1-c1nn[nH]n1]

A mixture of 2-bromo-4-chloro-6-fluoro-benzonitrile (4 g, 17.06 mmol) and azidotrimethyltin (3.86 g, 18.77 mmol) in toluene (100 ml) was heated to 120° C. for 72 h. After completion of the reaction, the mixture was partitioned between EtOAc (50 ml) and aqueous 0.5N HCl solution (40 ml). The organic layer was separated, washed with water and brine, dried with Na$_2$SO$_4$ and concentrated under reduced pressure to afford the title compound as red solid (4.2 g, 87%).

Step C: 5-(2-Bromo-4-chloro-6-fluoro-phenyl)-2-methyl-2H-tetrazole

A mixture of 5-(2-bromo-4-chloro-6-fluoro-phenyl)-2H-tetrazole (4.15 g, 14.95 mmol), K$_2$CO$_3$ (3.1 g, 22.43 mmol) and iodomethane (1.3 ml, 20.94 mmol) in DMF (30 ml) was stirred at 25° C. for 3 h. The mixture was partitioned between EtOAc (80 ml) and water (60 ml), the organic layer was separated, washed with water and brine, dried with Na$_2$SO$_4$ and concentrated. The remaining residue was purified by chromatography (silica gel; hexane/EtOAc 100:0-90:10) to obtain 5-(2-bromo-4-chloro-6-fluoro-phenyl)-1-methyl-1H-tetrazole as pale yellow solid (1.5 g, 35%) and the title compound as reddish liquid (1.7 g, 39%). MS: 291.0 [M+H]+.

Intermediate 12

N—[(R)-1-(5-Bromo-3-fluoro-pyridin-2-yl)-ethyl]-acetamide

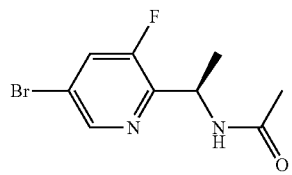

Step A: 2,5-Dibromo-3-nitro-pyridine

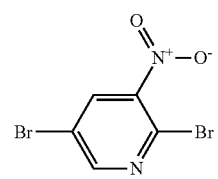

To a suspension 5-bromo-3-nitro-pyridin-2-ol (20 g, 91.32 mmol) in toluene (100 ml) was added DMF (0.7 ml, 9.13 mmol) and the mixture was heated to 90° C. (the reaction mixture was protected from light). A solution of POBr$_3$ (31.41 g, 109.51 mmol) in toluene (40 ml) was added dropwise at 90° C. and the reaction mixture was stirred at that temperature for 16 h. The mixture was allowed to cool to room temperature and toluene (50 ml) and water (50 ml) were added. The organic layer was separated, washed successively with aqueous 1N NaOH (60 ml), water (60 ml) and brine (30 ml), dried with Na$_2$SO$_4$ and evaporated obtain the title compound as yellow solid (25.2 g, 97%).

Step B: 5-Bromo-3-nitro-pyridine-2-carbonitrile

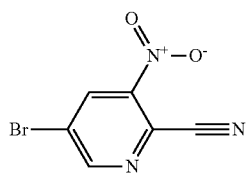

To a stirred solution of 2,5-dibromo-3-nitro-pyridine (25 g, 88.68 mmol) in propionitrile (100 ml) was added CuCN (8.7 g, 97.55 mmol) and the mixture was heated to 90° C. for 17 h. Then it was allowed to cool to room temperature, diluted with EtOAc, washed twice with brine, dried with Na$_2$SO$_4$ and concentrated. The remaining residue was purified by chromatography (silica gel; DCM/MeOH 95:5-85:15) to obtain the title compound as yellow solid (17.5 g, 68%).

Step C: 5-Bromo-3-fluoro-pyridine-2-carbonitrile

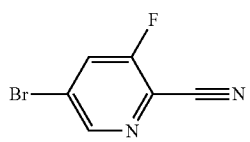

To a mixture of H$_2$SO$_4$ (0.2 ml) and TBAF solution (131 ml, 131 mmol, 1M in THF) was added DMF (40 ml) dropwise at −40° C. Then a solution of 5-bromo-3-nitro-pyridine-2-carbonitrile (10 g, 43 mmol) in DMF (130 ml) was added at −40° C. and the reaction mixture was stirred for 1 h. The reaction was then quenched by addition of 2M HCl solution at −40° C. adjusting the pH to 3. The resulting mixture was extracted twice with EtOAc and the combined organic extracts were washed twice with water, with brine, dried with Na$_2$SO$_4$ and evaporated in vacuo. The remaining residue was purified by chromatography (silica gel; hexane/EtOAc 90:10-80:20) to obtain the title compound as yellow solid (5.2 g, 59%).

Step D: N-[1-(5-Bromo-3-fluoro-pyridin-2-yl)-vinyl]-acetamide

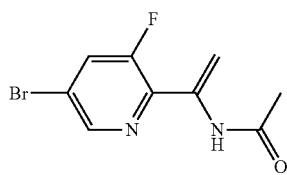

To a solution of 5-bromo-3-fluoro-pyridine-2-carbonitrile (10 g, 49.75 mmol) in toluene (50 ml) was added MeMgCl (24.87 ml, 74.62 mmol, 3M in THF) slowly at −10° C. The reaction mixture was stirred at −10° C. for 1 h, then acetic acid anhydride (47 ml, 497.5 mmol) was added and stirring was continued for 16 h at 25° C. The reaction was then quenched by addition of saturated aqueous NaHCO$_3$ solution (100 ml) and the resulting mixture was stirred for another 30 minutes. The organic layer was separated, washed twice with water, with brine, dried with Na$_2$SO$_4$ and evaporated. The remaining residue was purified by chromatography (silica gel; hexane/EtOAc 85:15-80:20) to obtain the title compound as brown solid (8.9 g, 69%).

Step E: N—[(R)-1-(5-Bromo-3-fluoro-pyridin-2-yl)-ethyl]acetamide

In a glovebox [Rh(COD)$_2$]BF$_4$ (96.76 mg, 238 μmol) and (S,S,R,R)-Tangphos (75.00 mg, 262 μmol) were dissolved in methanol (20 ml) and the mixture was stirred for 30 min. The resulting orange solution was transferred with additional methanol (30 ml) to a solution of N-[4-(5-bromo-3-fluoro-pyridin-2-yl)-vinyl]-acetamide (12.50 g, 47.6 mmol) in methanol (50 ml) in an autoclave. The reaction mixture was degassed with hydrogen (10 bar, 3 times) and then a final hydrogen pressure of 10 bar was applied for 3.5 h. Then charcoal (1.2 g) was added and the mixture was stirred for 1 h. After filtration through a pad of celite the filtrate was evaporated and the remaining solid was purified by chromatography (silica gel; DCM/EtOAc 90:10-50:50) to obtain the title compound as brown solid (10.38 g, 83%). MS: 261.0 [M+H]$^+$.

Intermediate 13

{(R)-1-[2-Fluoro-4-(4,4,5,5-tetramethyl-[1,3,2]diox-aborolan-2-yl)-phenyl]-ethyl}-carbamic acid tert-butyl ester

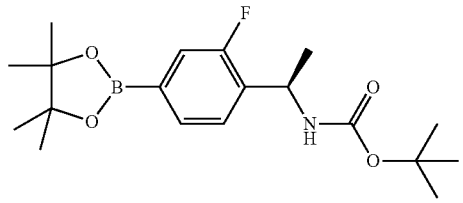 [SMILES: C[C@@H](NC(=O)OC(C)(C)C)c1ccc(B2OC(C)(C)C(C)(C)O2)cc1F]

Step A: (S)-2-Methyl-propane-2-sulfinic acid 1-(4-bromo-2-fluoro-phenyl)-meth-(E)-ylideneamide

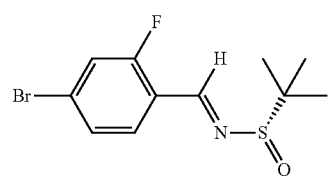 [SMILES: CC(C)(C)[S@](=O)/N=C/c1ccc(Br)cc1F]

To a solution of (S)-2-methylpropane-2-sulfinamide (4 g, 33.0 mmol) and 4-bromo-2-fluorobenzaldehyde (7.03 g, 34.7 mmol) in DCM (80.0 ml) were added pyridinium p-toluenesulfonate (415 mg, 1.65 mmol) and magnesium sulfate (39.7 g, 330 mmol) and the reaction mixture was stirred at room temperature over night. Then additional magnesium sulfate (19.85 g, 165 mmol) was added and stirring was continued for 24 h. The reaction mixture was filtered through a pad of celite and the filtrate was evaporated. The remaining light yellow oil was purified by chromatography (silica gel; heptane/EtOAc 95:5-90:10) to obtain the title compound as colorless oil (4.5 g, 44%).

Step B: (S)-2-Methyl-propane-2-sulfinic acid [(R)-1-(4-bromo-2-fluoro-phenyl)-ethyl]amide

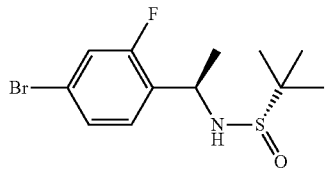 [SMILES: C[C@@H](N[S@@](=O)C(C)(C)C)c1ccc(Br)cc1F]

To a solution of (S)-2-methyl-propane-2-sulfinic acid 1-(4-bromo-2-fluoro-phenyl)-meth-(E)-ylideneamide (4.5 g, 14.7 mmol) in DCM (80 ml) was added methylmagnesium chloride (7.35 ml, 22.0 mmol, 3M solution in ether) dropwise at −48° C. After 1 h additional methylmagnesium chloride (2.45 ml, 7.35 mmol, 3M solution in ether) was added dropwise and the reaction mixture was stirred at −48° C. for 6 h. The reaction was then quenched by addition of sat. NH$_4$Cl solution and the mixture was extracted three times with DCM. The combined organic layers were dried with Na$_2$SO$_4$ and evaporated. The remaining white solid was purified by chromatography (silica gel; heptane/EtOAc 2:1-1:1) to obtain the title compound as white solid (3.89 g, 82%).

Step C: (R)-1-(4-Bromo-2-fluoro-phenyl)-ethylamine hydrochloride

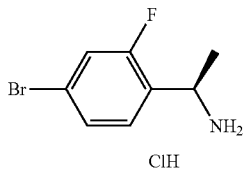

To a solution of (S)-2-methyl-propane-2-sulfinic acid [(R)-1-(4-bromo-2-fluoro-phenyl)-ethyl]-amide (4.02 g, 12.5 mmol) in methanol (25 ml) was added a 4M HCl solution in dioxane (6.24 ml, 25.0 mmol) and the mixture was stirred for 4 h. The reaction mixture was then concentrated and diethyl ether was added. The resulting suspension was stirred for 2 h and then filtered to deliver the title compound as white solid (3.11 g, 98%).

Step D: [(R)-1-(4-Bromo-2-fluoro-phenyl)-ethyl] carbamic acid tert-butyl ester

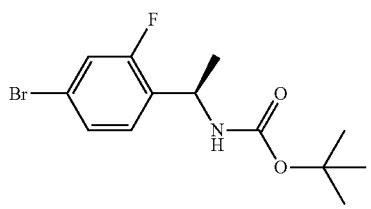 [SMILES: C[C@@H](NC(=O)OC(C)(C)C)c1ccc(Br)cc1F]

To a suspension of (R)-1-(4-bromo-2-fluoro-phenyl)-ethylamine hydrochloride (3.11 g, 12.2 mmol) in DCM (30 ml) were added di-tert-butyl dicarbonate (4.00 g, 4.26 ml, 18.3 mmol) and triethylamine (1.79 g, 2.47 ml, 17.7 mmol) at 0° C. The reaction mixture was allowed to warm to room temperature and was stirred for 20 h. Then water was added and the mixture was extracted three times with DCM. The combined organic extracts were washed with water and brine, dried with Na$_2$SO$_4$ and concentrated. The remaining off-white solid was purified by chromatography (silica gel; heptane/EtOAc 70:30-50:50) to obtain the title compound as white solid (4.7 g, 90%).

Step E: {(R)-1-[2-Fluoro-4-(4,4,5,5-tetramethyl-[1,3,2]dioxaborolan-2-yl)-phenyl]-ethyl}-carbamic acid tert-butyl ester A mixture of [(R)-1-(4-bromo-2-fluoro-phenyl)-ethyl]carbamic acid tert-butyl ester (4.7 g, 13.1 mmol), bis(pinacolato)diboron (5.01 g, 19.7 mmol), [1,1'-bis(diphenylphosphino)ferrocene]palladium(II) chloride 1:1 complex with DCM (107 mg, 131 μmol) and potassium acetate (3.87 g, 39.4 mmol) in DMSO (30 ml) was stirred at 90° C. for 50 h. The reaction mixture was allowed to cool to room temperature, water was added and the mixture was extracted three times with EtOAc. The combined organic extracts were washed with water and brine, dried with Na$_2$SO$_4$ and concentrated. The remaining residue was purified by chromatography (silica gel; heptane/EtOAc 70:30-60:40) to obtain the title compound as light yellow solid (4.6 g, 95%). MS: 366.3 [M+H]$^+$.

Intermediate 14

3-Methoxy-isoxazole-5-carboxylic acid

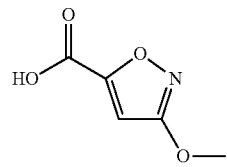

To a solution of methyl 3-hydroxyisoxazole-5-carboxylate (958 mg, 6.69 mmol) in DMF (10 ml) was added potassium carbonate (935 mg, 6.76 mmol) at −5° C. Then dimethyl sulfate (644 μL, 6.76 mmol) was added slowly. The reaction mixture was allowed to warm to room temperature and was stirred over night. Then 2N NaOH (5.02 mL, 10.0 mmol) was added and the mixture was stirred for 4 h. After slow addition of 2N HCl (6.69 mL, 13.4 mmol), the mixture was extracted three times with diethyl ether. The combined organic extracts were washed with brine and evaporated. The remaining yellow oil was co-evaporated four times with toluene to give a solid that was dried for 4 h at 40° C. under high vacuum. The title compound as obtained as light brown solid (576 mg, 60%).

Example 1

3-(3-Fluoro-5-trifluoromethyl-benzoylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide

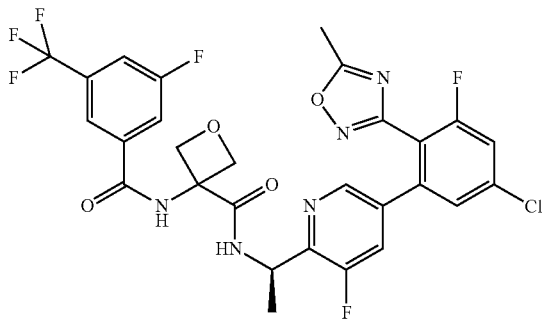 [SMILES: Cc1nc(-c2c(F)cc(Cl)cc2-c2cnc([C@@H](C)NC(=O)C3(NC(=O)c4cc(F)cc(C(F)(F)F)c4)COC3)c(F)c2)no1]

3-Amino-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide (30.0 mg, 0.0667 mmol, intermediate 1) was dissolved in dry DMF (1.5 ml) and 3-fluoro-5-(trifluoromethyl)benzoic acid (17.0 mg, 0.0800 mmol), 1-hydroxybenzotriazole hydrate (11.2 mg, 0.0734 mmol), triethylamine (13.5 mg, 18.5 µl, 0.133 mmol) and N-(3-dimethylaminopropyl)-N'-ethylcarbodiimide hydrochloride (26.0 mg, 0.133 mmol) were added. The colorless solution was stirred at room temperature overnight. Then water was added and the mixture was extracted three times with EtOAc. The combined organic layers were washed with sat. NaHCO$_3$ solution, sat. NH$_4$Cl solution, water and brine, dried with Na$_2$SO$_4$ and evaporated.

The remaining light yellow gum was purified by chromatography (silica gel; DCM/MeOH 98:2) and the title compound was obtained as white foam (38 mg, 89%). MS: 640.1 [M+H]$^+$.

Example 2

3-(2,2,2-Trifluoro-acetylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide

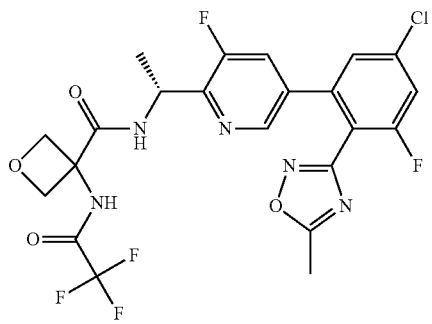 [SMILES: Cc1nc(-c2c(F)cc(Cl)cc2-c2cnc([C@@H](C)NC(=O)C3(NC(=O)C(F)(F)F)COC3)c(F)c2)no1]

Trifluoroacetic anhydride (15.9 mg, 10.5 µl, 0.0756 mmol) was added slowly to a solution of 3-amino-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide (34.0 mg, 0.0756 mmol) and triethylamine (8.42 mg, 11.6 µl, 0.0832 mmol) in DCM (2 ml) at 0° C. After the addition, the colorless solution was stirred at 0° C.-5° C. for 45 min and then at room temperature over night. Additional triethylamine (1.53 mg, 2.1 µl, 0.0151 mmol) and trifluoroacetic anhydride (3.17 mg, 2.1 µl, 0.0151 mmol) were added and the mixture was stirred for 2 h. The solution was then diluted with DCM and sat. Na$_2$CO$_3$ solution. The layers were separated and the aqueous layer was extracted with DCM. The combined organic layers were dried with Na$_2$SO$_4$ and evaporated. The remaining colorless gum was purified by chromatography (silica gel; DCM/MeOH 98:2-95:5) and the title compound was obtained as white foam (14 mg, 34%). MS: 546.2 [M+H]$^+$.

Example 3

Isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

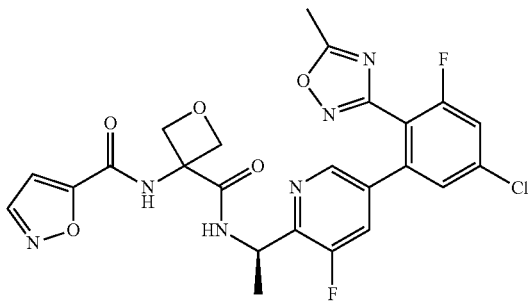 [SMILES: Cc1nc(-c2c(F)cc(Cl)cc2-c2cnc([C@@H](C)NC(=O)C3(NC(=O)c4ccno4)COC3)c(F)c2)no1]

The title compound was prepared in analogy to example 1 using isoxazole-5-carboxylic acid instead of 3-fluoro-5-(trifluoromethyl)benzoic acid and was obtained as white foam. MS: 545.3 [M+H]$^+$.

Example 4

3-Methyl-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

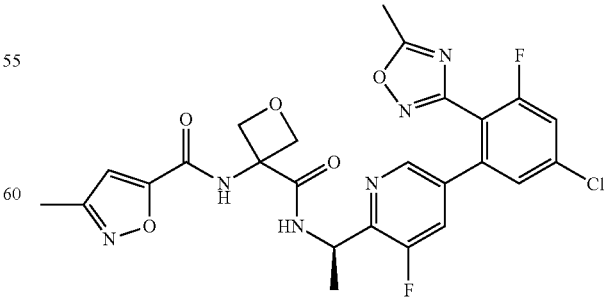

The title compound was prepared in analogy to example 1 using 3-methylisoxazole-5-carboxylic acid instead of 3-fluoro-5-(trifluoromethyl)benzoic acid and was obtained as white foam. MS: 559.1 [M+H]+.

Example 5

Pyrimidine-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

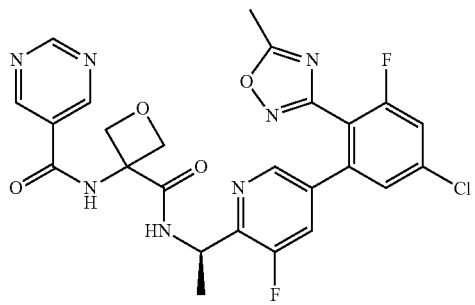 [SMILES: Cc1nc(-c2c(F)cc(Cl)cc2-c2cnc([C@@H](C)NC(=O)C3(NC(=O)c4cncnc4)COC3)c(F)c2)no1]

The title compound was prepared in analogy to example 1 using pyrimidine-5-carboxylic acid instead of 3-fluoro-5-(trifluoromethyl)benzoic acid and was obtained as off white foam. MS: 556.2 [M+H]+.

Example 6

3-Chloro-3'-fluoro-4'-((R)-1-{[3-(2,2,2-trifluoro-acetylamino)-oxetane-3-carbonyl]-amino}-ethyl)-biphenyl-2-carboxylic acid methyl ester

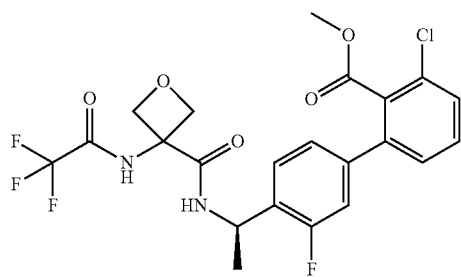 [SMILES: COC(=O)c1c(Cl)cccc1-c1ccc([C@@H](C)NC(=O)C2(NC(=O)C(F)(F)F)COC2)c(F)c1]

The title compound was prepared in analogy to example 2 using intermediate 4 instead of intermediate 1 and was obtained as white solid. MS: 501.0 [M−H]−.

Example 7

3-Chloro-3'-fluoro-4'-[(R)-1-({3-[(pyrimidine-5-carbonyl)-amino]-oxetane-3-carbonyl}-amino)-ethyl]-biphenyl-2-carboxylic acid methyl ester

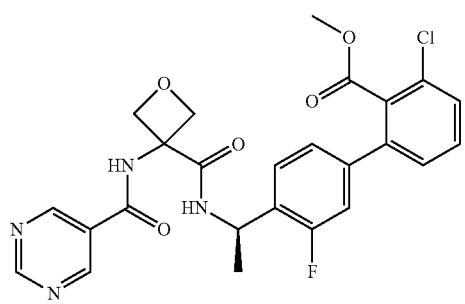 [SMILES: COC(=O)c1c(Cl)cccc1-c1ccc([C@@H](C)NC(=O)C2(NC(=O)c3cncnc3)COC2)c(F)c1]

The title compound was prepared in analogy to example 1 using intermediate 4 instead of intermediate 1 and pyrimidine-5-carboxylic acid instead of 3-fluoro-5-(trifluoromethyl)benzoic acid and was obtained as white solid. MS: 513.2 [M+H]+.

Example 8

3-Chloro-3'-fluoro-4'-((R)-1-{[3-(3,3,3-trifluoro-propionylamino)-oxetane-3-carbonyl]-amino}-ethyl)-biphenyl-2-carboxylic acid methyl ester

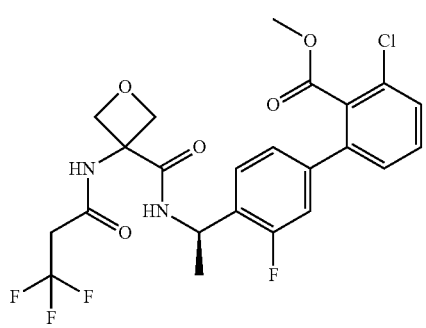 [SMILES: COC(=O)c1c(Cl)cccc1-c1ccc([C@@H](C)NC(=O)C2(NC(=O)CC(F)(F)F)COC2)c(F)c1]

The title compound was prepared in analogy to example 1 using intermediate 4 instead of intermediate 1 and 3,3,3-trifluoropropionic acid instead of 3-fluoro-5-(trifluoromethyl)benzoic acid and was obtained as white solid. 515.2 [M−H]−.

Example 9

3-Methyl-isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

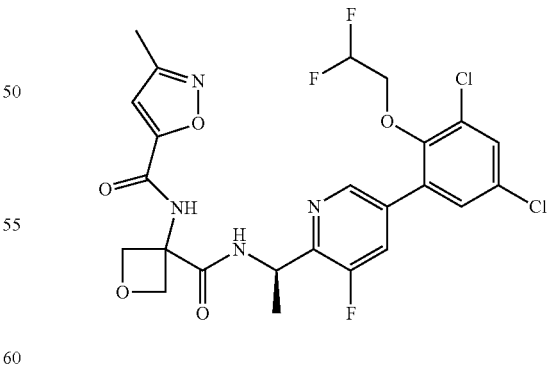

The title compound was prepared in analogy to example 1 using intermediate 2 instead of intermediate 1 and 3-methyl-isoxazole-5-carboxylic acid instead of 3-fluoro-5-(trifluoromethyl)benzoic acid and was obtained as white foam. MS: 571.1 [M−H]−.

Example 10

Isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

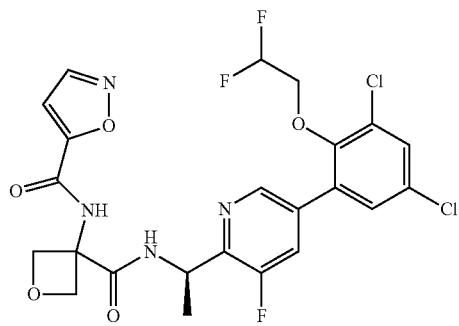 [SMILES: C[C@@H](NC(=O)C1(NC(=O)c2ccno2)COC1)c1ncc(-c2cc(Cl)cc(Cl)c2OCC(F)F)cc1F]

The title compound was prepared in analogy to example 1 using intermediate 2 instead of intermediate 1 and isoxazole-5-carboxylic acid instead of 3-fluoro-5-(trifluoromethyl)benzoic acid and was obtained as white foam. MS: 557.1 [M−H]⁻.

Example 11

Pyrimidine-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

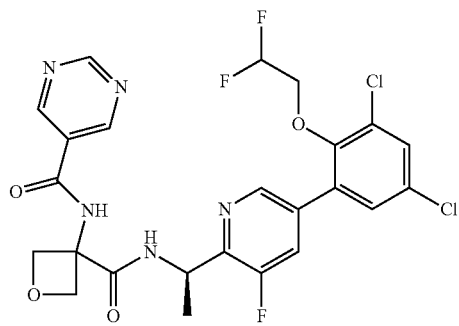 [SMILES: C[C@@H](NC(=O)C1(NC(=O)c2cncnc2)COC1)c1ncc(-c2cc(Cl)cc(Cl)c2OCC(F)F)cc1F]

The title compound was prepared in analogy to example 1 using intermediate 2 instead of intermediate 1 and pyrimidine-5-carboxylic acid instead of 3-fluoro-5-(trifluoromethyl)benzoic acid and was obtained as white foam. MS: 570.0 [M+H]⁺.

Example 12

3-Chloro-3'-fluoro-4'-[(R)-1-({3-[(isoxazole-5-carbonyl)-amino]-oxetane-3-carbonyl}-amino)-ethyl]-biphenyl-2-carboxylic acid methyl ester

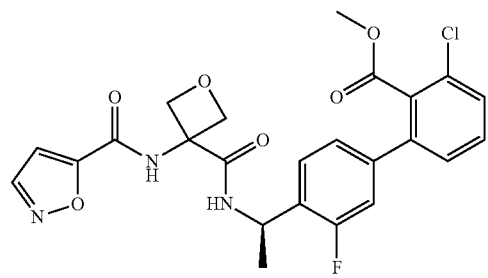 [SMILES: COC(=O)c1c(Cl)cccc1-c1ccc([C@@H](C)NC(=O)C2(NC(=O)c3ccno3)COC2)c(F)c1]

The title compound was prepared in analogy to example 1 using intermediate 4 instead of intermediate 1 and isoxazole-5-carboxylic acid instead of 3-fluoro-5-(trifluoromethyl)benzoic acid and was obtained as white solid. MS: 502.1 [M+H]⁺.

Example 13

3-Chloro-3'-fluoro-4'-[(R)-1-({3-[(3-methyl-isoxazole-5-carbonyl)-amino]-oxetane-3-carbonyl}-amino)-ethyl]-biphenyl-2-carboxylic acid methyl ester

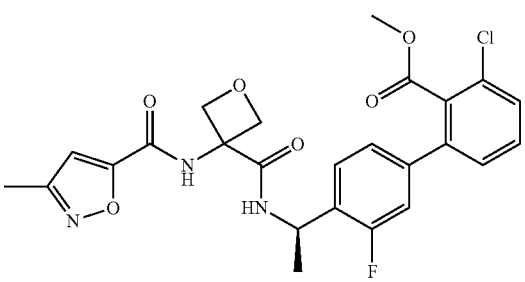 [SMILES: COC(=O)c1c(Cl)cccc1-c1ccc([C@@H](C)NC(=O)C2(NC(=O)c3cc(C)no3)COC2)c(F)c1]

The title compound was prepared in analogy to example 1 using intermediate 4 instead of intermediate 1 and 3-methyl-isoxazole-5-carboxylic acid instead of 3-fluoro-5-(trifluoromethyl)benzoic acid and was obtained as white solid. MS: 516.1 [M+H]⁺.

Example 14

3-Methoxy-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

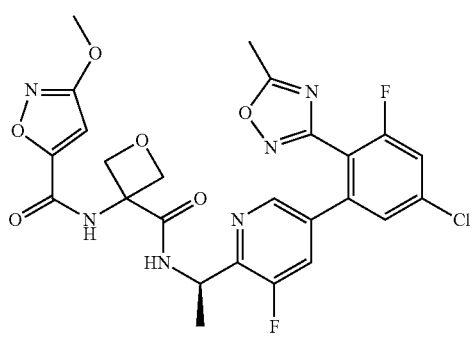 [SMILES: COc1cc(C(=O)NC2(C(=O)N[C@H](C)c3ncc(-c4cc(Cl)cc(F)c4-c4noc(C)n4)cc3F)COC2)on1]

The title compound was prepared in analogy to example 1 using 3-methoxy-isoxazole-5-carboxylic acid (intermediate 14) instead of 3-fluoro-5-(trifluoromethyl)benzoic acid and was obtained as off white foam. MS: 575.2 [M+H]⁺.

Example 15

2-Methoxy-pyrimidine-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

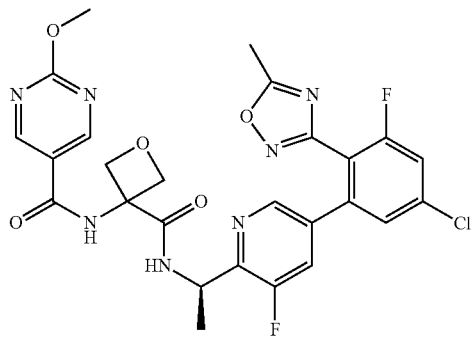 [SMILES: COc1ncc(C(=O)NC2(C(=O)N[C@H](C)c3ncc(-c4cc(Cl)cc(F)c4-c4noc(C)n4)cc3F)COC2)cn1]

The title compound was prepared in analogy to example 1 using 2-methoxypyrimidine-5-carboxylic acid instead of 3-fluoro-5-(trifluoromethyl)benzoic acid and was obtained as light brown foam. MS: 586.1 [M+H]$^+$.

Example 16

4-Methyl-[1,2,3]thiadiazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

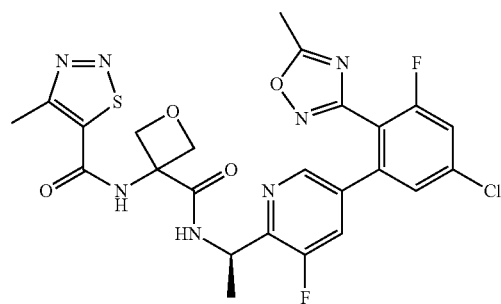 [SMILES: Cc1nc(-c2c(F)cc(Cl)cc2-c2cnc([C@@H](C)NC(=O)C3(NC(=O)c4snnc4C)COC3)c(F)c2)no1]

The title compound was prepared in analogy to example 1 using 4-methyl-1,2,3-thiadiazole-5-carboxylic acid instead of 3-fluoro-5-(trifluoromethyl)benzoic acid and was obtained as white foam. MS: 576.2 [M+H]$^+$.

Example 17

3-(2-Methoxy-acetylamino)-oxetane-3-carboxylic acid ((R)-1-{5-[5-chloro-3-fluoro-2-(5-methyl-[1,2,4]oxadiazol-3-yl)-phenyl]-3-fluoro-pyridin-2-yl}-ethyl)-amide

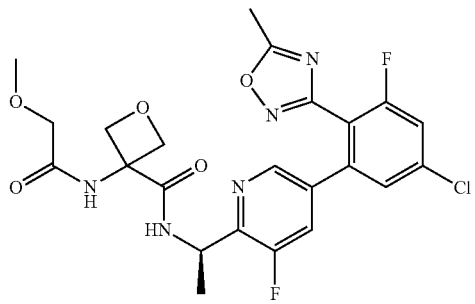 [SMILES: COCC(=O)NC1(C(=O)N[C@H](C)c2ncc(-c3cc(Cl)cc(F)c3-c3noc(C)n3)cc2F)COC1]

The title compound was prepared in analogy to example 1 using 2-methoxyacetic acid instead of 3-fluoro-5-(trifluoromethyl)benzoic acid and was obtained as white foam. MS: 522.2 [M+H]$^+$.

Example 18

3-Methoxy-isoxazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

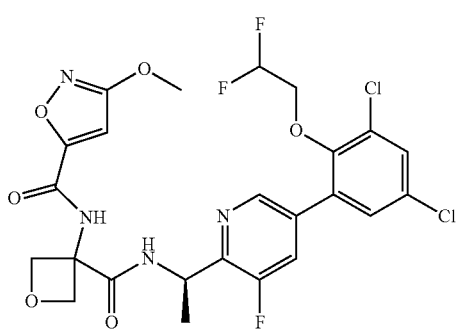 [SMILES: COc1cc(C(=O)NC2(C(=O)N[C@H](C)c3ncc(-c4cc(Cl)cc(Cl)c4OCC(F)F)cc3F)COC2)on1]

The title compound was prepared in analogy to example 1 using intermediate 2 instead of intermediate 1 and 3-methoxy-isoxazole-5-carboxylic acid (intermediate 14) instead of 3-fluoro-5-(trifluoromethyl)benzoic acid and was obtained as white solid. MS: 589.2 [M+H]$^+$.

Example 19

5-Methyl-[1,3,4]oxadiazole-2-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

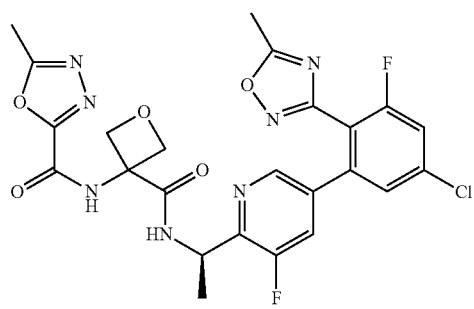 [SMILES: Cc1nc(-c2c(F)cc(Cl)cc2-c2cnc([C@@H](C)NC(=O)C3(NC(=O)c4nnc(C)o4)COC3)c(F)c2)no1]

The title compound was prepared in analogy to example 1 using 5-methyl-1,3,4-oxadiazole-2-carboxylic acid instead of 3-fluoro-5-(trifluoromethyl)benzoic acid and was obtained as white foam. MS: 560.2 [M+H]$^+$.

Example 20

3-Methyl-isoxazole-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide

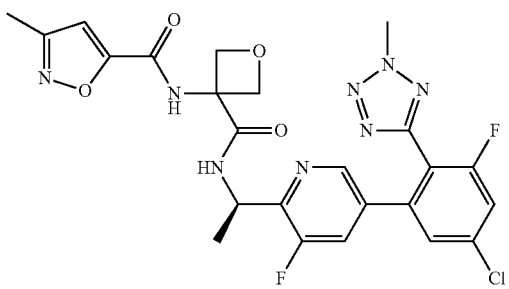 [SMILES: Cc1cc(C(=O)NC2(C(=O)N[C@H](C)c3ncc(-c4cc(Cl)cc(F)c4-c4nnn(C)n4)cc3F)COC2)on1]

The title compound was prepared in analogy to example 1 using intermediate 3 instead of intermediate 1 and 3-methyl-isoxazole-5-carboxylic acid instead of 3-fluoro-5-(trifluoromethyl)benzoic acid and was obtained as white solid. MS: 559.1 [M+H]$^+$.

Example 21

3-(2,2,2-Trifluoro-acetylamino)-oxetane-3-carboxylic acid ((R)-1-{5-[5-chloro-3-fluoro-2-(2-methyl-2H-tetrazol-5-yl)-phenyl]-3-fluoro-pyridin-2-yl}-ethyl)-amide

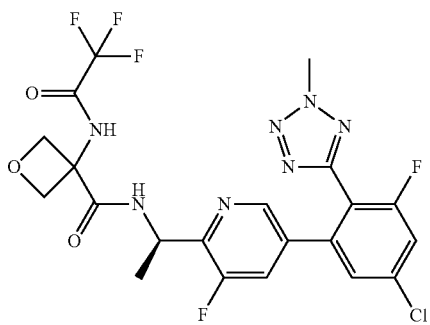 [SMILES: C[C@@H](NC(=O)C1(NC(=O)C(F)(F)F)COC1)c1ncc(-c2cc(Cl)cc(F)c2-c2nnn(C)n2)cc1F]

The title compound was prepared in analogy to example 2 using intermediate 3 instead of intermediate 1 and was obtained as white solid. MS: 546.1 [M+H]$^+$.

Example 22

3-(2,2,2-Trifluoro-acetylamino)-oxetane-3-carboxylic acid {(R)-1-[5'-chloro-3,3'-difluoro-2'-(2-methyl-2H-tetrazol-5-yl)-biphenyl-4-yl]-ethyl}-amide

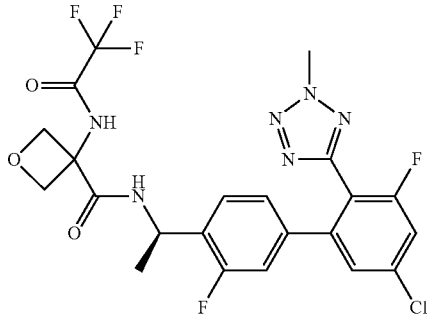 [SMILES: C[C@@H](NC(=O)C1(NC(=O)C(F)(F)F)COC1)c1ccc(-c2cc(Cl)cc(F)c2-c2nnn(C)n2)cc1F]

The title compound was prepared in analogy to example 2 using intermediate 5 instead of intermediate 1 and was obtained as white solid. MS: 545.1 [M+H]$^+$.

Example 23

3-Methyl-isoxazole-5-carboxylic acid (3-{(R)-1-[5'-chloro-3,3'-difluoro-2'-(2-methyl-2H-tetrazol-5-yl)-biphenyl-4-yl]-ethylcarbamoyl}-oxetan-3-yl)-amide

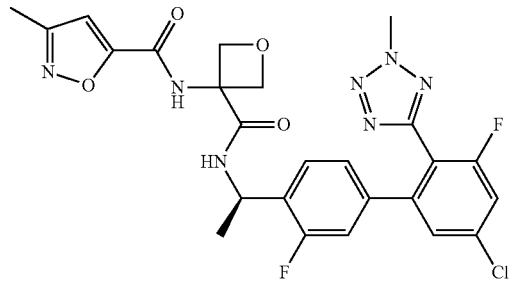 [SMILES: Cc1cc(C(=O)NC2(C(=O)N[C@H](C)c3ccc(-c4cc(Cl)cc(F)c4-c4nnn(C)n4)cc3F)COC2)on1]

The title compound was prepared in analogy to example 1 using intermediate 5 instead of intermediate 1 and 3-methyl-isoxazole-5-carboxylic acid instead of 3-fluoro-5-(trifluoromethyl)benzoic acid and was obtained as white solid. MS: 558.1 [M+H]$^+$.

Example 24

3-Methyl-isoxazole-5-carboxylic acid (3-{(R)-1-[5'-chloro-3,3'-difluoro-2'-(5-methyl-[1,2,4]oxadiazol-3-yl)-biphenyl-4-yl]-ethylcarbamoyl}-oxetan-3-yl)-amide

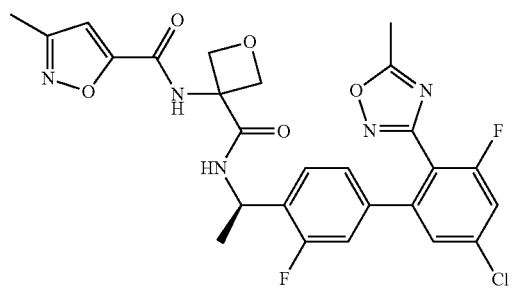 [SMILES: Cc1cc(C(=O)NC2(C(=O)N[C@H](C)c3ccc(-c4cc(Cl)cc(F)c4-c4noc(C)n4)cc3F)COC2)on1]

The title compound was prepared in analogy to example 1 using intermediate 6 instead of intermediate 1 and 3-methyl-isoxazole-5-carboxylic acid instead of 3-fluoro-5-(trifluoromethyl)benzoic acid and was obtained as white foam. MS: 558.2 [M+H]$^+$.

Example 25

Pyridazine-4-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

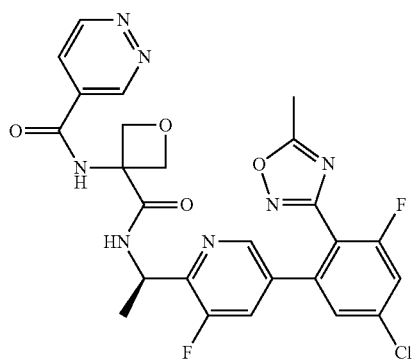 [SMILES: Cc1nc(-c2c(F)cc(Cl)cc2-c2cnc([C@@H](C)NC(=O)C3(NC(=O)c4ccnnc4)COC3)c(F)c2)no1]

The title compound was prepared in analogy to example 1 using pyridazine-4-carboxylic acid instead of 3-fluoro-5-(trifluoromethyl)benzoic acid and was obtained as white foam. MS: 556.1 [M+H]⁺.

Example 26

1-Methyl-1H-imidazole-2-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

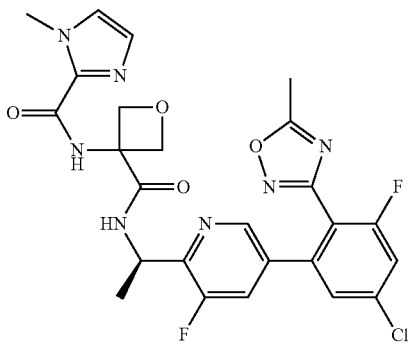 [SMILES: Cc1nc(-c2c(F)cc(Cl)cc2-c2cnc([C@@H](C)NC(=O)C3(NC(=O)c4nccn4C)COC3)c(F)c2)no1]

The title compound was prepared in analogy to example 1 using 1-methyl-1H-imidazole-2-carboxylic acid instead of 3-fluoro-5-(trifluoromethyl)benzoic acid and was obtained as white foam. MS: 558.2 [M+H]⁺.

Example 27

1-Methyl-1H-imidazole-4-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

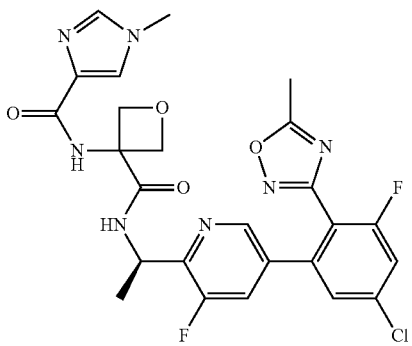 [SMILES: Cc1nc(-c2c(F)cc(Cl)cc2-c2cnc([C@@H](C)NC(=O)C3(NC(=O)c4cn(C)cn4)COC3)c(F)c2)no1]

The title compound was prepared in analogy to example 1 using 1-methyl-1H-imidazole-4-carboxylic acid instead of 3-fluoro-5-(trifluoromethyl)benzoic acid and was obtained as off-white foam. MS: 558.0 [M+H]⁺.

Example 28

5-Amino-N-[3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-nicotinamide

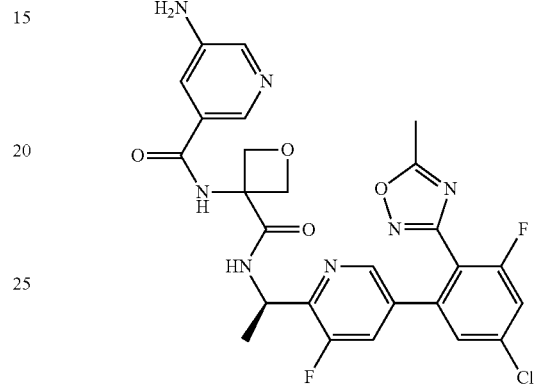

The title compound was prepared in analogy to example 1 using 5-amino-nicotinic acid instead of 3-fluoro-5-(trifluoromethyl)benzoic acid and was obtained as off-white foam. MS: 570.1 [M+H]⁺.

Example 29

Pyridazine-3-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide

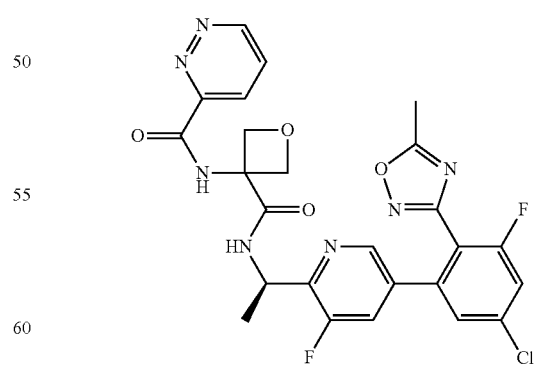

The title compound was prepared in analogy to example 1 using pyridazine-3-carboxylic acid instead of 3-fluoro-5-(trifluoromethyl)benzoic acid and was obtained as off-white foam. MS: 556.2 [M+H]⁺.

Example 30
N-[3-((R)-1-{5-[5-Chloro-3-fluoro-2-(5-methyl-[1,2,4]oxadiazol-3-yl)-phenyl]-3-fluoro-pyridin-2-yl}-ethylcarbamoyl)-oxetan-3-yl]-nicotinamide

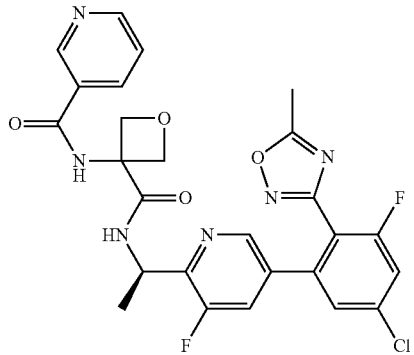 [SMILES: Cc1nc(-c2c(F)cc(Cl)cc2-c2cnc([C@@H](C)NC(=O)C3(NC(=O)c4cccnc4)COC3)c(F)c2)no1]

The title compound was prepared in analogy to example 1 using nicotinic acid instead of 3-fluoro-5-(trifluoromethyl) benzoic acid and was obtained as light yellow foam. MS: 555.3 [M+H]⁺.

Example 31
2-Methoxy-pyrimidine-5-carboxylic acid (3-{(R)-1-[5'-chloro-3,3'-difluoro-2'-(5-methyl-[1,2,4]oxadiazol-3-yl)-biphenyl-4-yl]-ethylcarbamoyl}-oxetan-3-yl)-amide

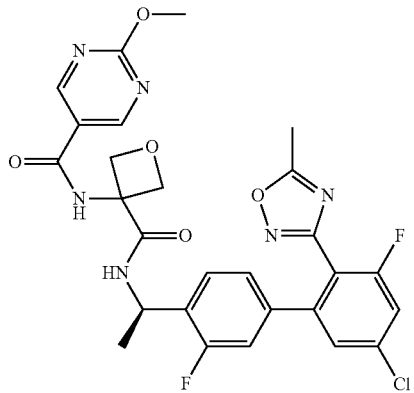 [SMILES: COc1ncc(C(=O)NC2(C(=O)N[C@H](C)c3ccc(-c4cc(Cl)cc(F)c4-c4noc(C)n4)cc3F)COC2)cn1]

The title compound was prepared in analogy to example 1 using intermediate 6 instead of intermediate 1 and 2-methoxy-pyrimidine-5-carboxylic acid instead of 3-fluoro-5-(trifluoromethyl)benzoic acid and was obtained as off-white foam. MS: 585.2 [M+H]⁺.

Example 32
Isoxazole-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide

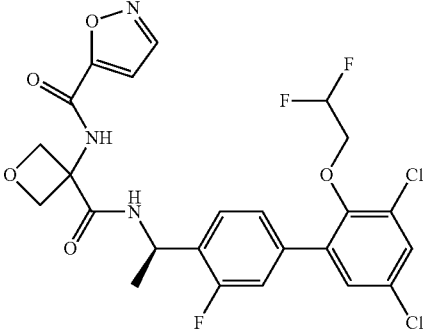 [SMILES: C[C@@H](NC(=O)C1(NC(=O)c2ccno2)COC1)c1ccc(-c2cc(Cl)cc(Cl)c2OCC(F)F)cc1F]

The title compound was prepared in analogy to example 1 using intermediate 7 instead of intermediate 1 and isoxazole-5-carboxylic acid instead of 3-fluoro-5-(trifluoromethyl)benzoic acid and was obtained as white solid. MS: 556.1 [M−H]⁻.

Example 33
3-(2,2,2-Trifluoro-acetylamino)-oxetane-3-carboxylic acid {(R)-1-[3',5'-dichloro-2'-(2,2-difluoro-ethoxy)-3-fluoro-biphenyl-4-yl]-ethyl}-amide

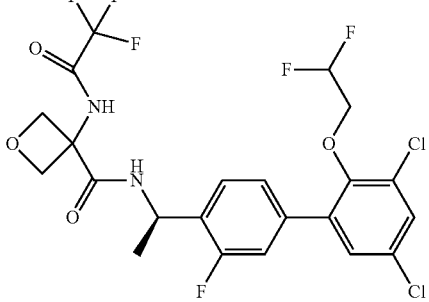

The title compound was prepared in analogy to example 2 using intermediate 7 instead of intermediate 1 and was obtained as white solid. MS: 559.1 [M+H]⁺.

Example 34
3-Methoxy-isoxazole-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide

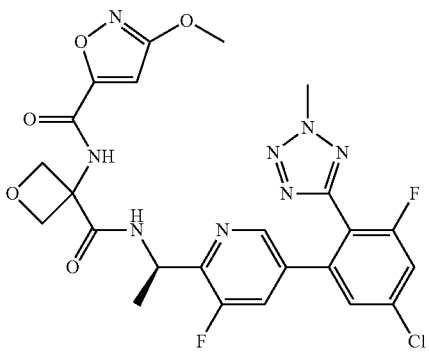 [SMILES: COc1cc(C(=O)NC2(C(=O)N[C@H](C)c3ncc(-c4cc(Cl)cc(F)c4-c4nnn(C)n4)cc3F)COC2)on1]

The title compound was prepared in analogy to example 1 using intermediate 3 instead of intermediate 1 and 3-methoxy-isoxazole-5-carboxylic acid (intermediate 14) instead of 3-fluoro-5-(trifluoromethyl)benzoic acid and was obtained as colorless oil. MS: 575.1 [M+H]⁺.

Example 35

2-Methoxy-pyrimidine-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide

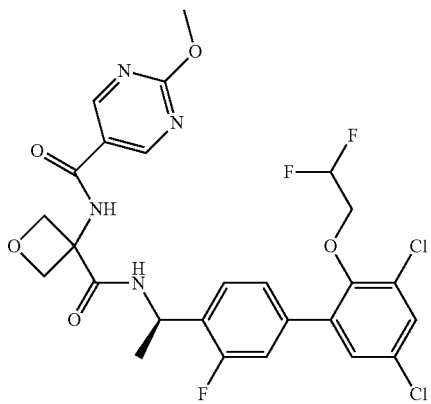 [SMILES: COc1ncc(C(=O)NC2(C(=O)N[C@H](C)c3ccc(-c4cc(Cl)cc(Cl)c4OCC(F)F)cc3F)COC2)cn1]

The title compound was prepared in analogy to example 1 using intermediate 7 instead of intermediate 1 and 2-methoxy-pyrimidine-5-carboxylic acid instead of 3-fluoro-5-(trifluoromethyl)benzoic acid and was obtained as colorless oil. MS: 599.1 [M+H]$^+$.

Example 36

2-Methoxy-pyrimidine-5-carboxylic acid [3-((R)-1-{5-[5-chloro-3-fluoro-2-(2-methyl-2H-tetrazol-5-yl)-phenyl]-3-fluoro-pyridin-2-yl}-ethylcarbamoyl)-oxetan-3-yl]-amide

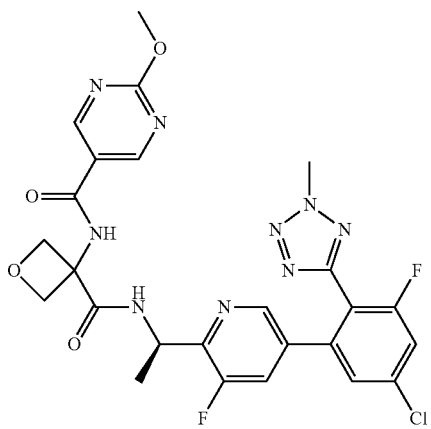 [SMILES: COc1ncc(C(=O)NC2(C(=O)N[C@H](C)c3ncc(-c4cc(Cl)cc(F)c4-c4nnn(C)n4)cc3F)COC2)cn1]

The title compound was prepared in analogy to example 1 using intermediate 3 instead of intermediate 1 and 2-methoxy-pyrimidine-5-carboxylic acid instead of 3-fluoro-5-(trifluoromethyl)benzoic acid and was obtained as white solid. MS: 586.1 [M+H]$^+$.

Example 37

3-Methoxy-isoxazole-5-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide

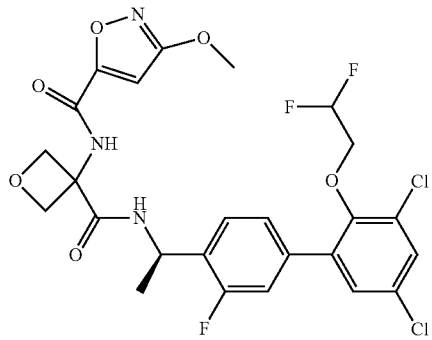 [SMILES: COc1cc(C(=O)NC2(C(=O)N[C@H](C)c3ccc(-c4cc(Cl)cc(Cl)c4OCC(F)F)cc3F)COC2)on1]

The title compound was prepared in analogy to example 1 using intermediate 7 instead of intermediate 1 and 3-methoxy-isoxazole-5-carboxylic acid (intermediate 14) instead of 3-fluoro-5-(trifluoromethyl)benzoic acid and was obtained as white solid. MS: 588.1 [M+H]$^+$.

Example 38

5-Methyl-[1,3,4]oxadiazole-2-carboxylic acid (3-{(R)-1-[3',5'-dichloro-2'-(2,2-difluoro-ethoxy)-3-fluoro-biphenyl-4-yl]-ethylcarbamoyl}-oxetan-3-yl)-amide

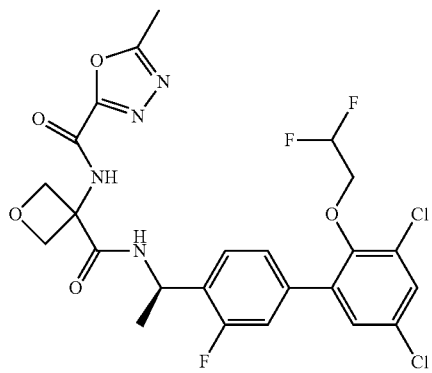 [SMILES: Cc1nnc(C(=O)NC2(C(=O)N[C@H](C)c3ccc(-c4cc(Cl)cc(Cl)c4OCC(F)F)cc3F)COC2)o1]

The title compound was prepared in analogy to example 1 using intermediate 7 instead of intermediate 1 and 5-methyl-1,3,4-oxadiazole-2-carboxylic acid instead of 3-fluoro-5-(trifluoromethyl)benzoic acid and was obtained as colorless oil. MS: 573.1 [M+H]$^+$.

Example 39

5-Methyl-[1,3,4]oxadiazole-2-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

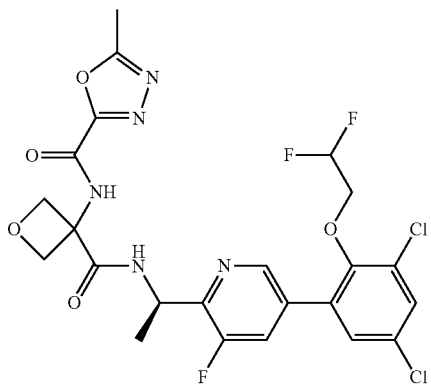 [SMILES: Cc1nnc(C(=O)NC2(C(=O)N[C@H](C)c3ncc(-c4cc(Cl)cc(Cl)c4OCC(F)F)cc3F)COC2)o1]

The title compound was prepared in analogy to example 1 using intermediate 2 instead of intermediate 1 and 5-methyl-1,3,4-oxadiazole-2-carboxylic acid instead of 3-fluoro-5-(trifluoromethyl)benzoic acid and was obtained as white solid. MS: 572.2 [M−H]⁻.

Example 40

2-Methoxy-pyrimidine-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

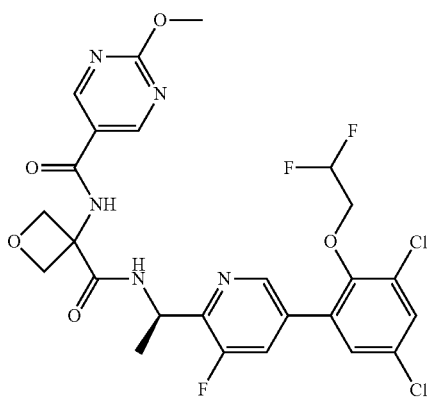 [SMILES: COc1ncc(C(=O)NC2(C(=O)N[C@H](C)c3ncc(-c4cc(Cl)cc(Cl)c4OCC(F)F)cc3F)COC2)cn1]

The title compound was prepared in analogy to example 1 using intermediate 2 instead of intermediate 1 and 2-methoxy-pyrimidine-5-carboxylic acid instead of 3-fluoro-5-(trifluoromethyl)benzoic acid and was obtained as white solid. MS: 600.0 [M+H]⁺.

Example 41

4-Methyl-[1,2,3]thiadiazole-5-carboxylic acid [3-((R)-1-{5-[3,5-dichloro-2-(2,2-difluoro-ethoxy)-phenyl]-3-fluoro-pyridin-2-yl}-ethylcarbamoyl)-oxetan-3-yl]-amide

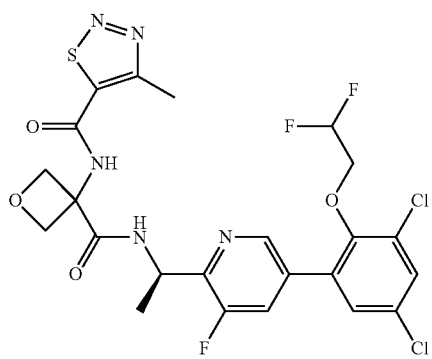 [SMILES: Cc1nnsc1C(=O)NC1(C(=O)N[C@H](C)c2ncc(-c3cc(Cl)cc(Cl)c3OCC(F)F)cc2F)COC1]

The title compound was prepared in analogy to example 1 using intermediate 2 instead of intermediate 1 and 4-methyl-1,2,3-thiadiazole-5-carboxylic acid instead of 3-fluoro-5-(trifluoromethyl)benzoic acid and was obtained as light yellow solid. MS: 590.2 [M+H]⁺.

Example 42

3-(2-Methoxy-acetylamino)-oxetane-3-carboxylic acid ((R)-1-{5-[3,5-dichloro-2-(2,2-difluoro-ethoxy)-phenyl]-3-fluoro-pyridin-2-yl}-ethyl)-amide

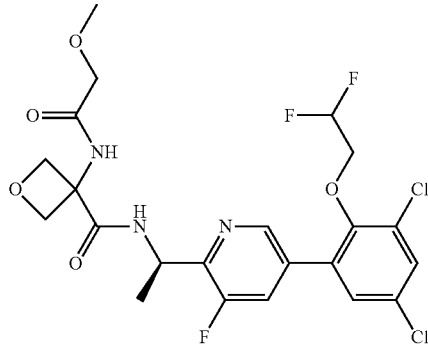 [SMILES: COCC(=O)NC1(C(=O)N[C@H](C)c2ncc(-c3cc(Cl)cc(Cl)c3OCC(F)F)cc2F)COC1]

The title compound was prepared in analogy to example 1 using intermediate 2 instead of intermediate 1 and 2-methoxyacetic acid instead of 3-fluoro-5-(trifluoromethyl)benzoic acid and was obtained as white solid. MS: 536.1 [M+H]⁺.

Example 43

3-Methoxy-isoxazole-5-carboxylic acid (3-{(R)-1-[5'-chloro-3,3'-difluoro-2'-(2-methyl-2H-tetrazol-5-yl)-biphenyl-4-yl]-ethylcarbamoyl}-oxetan-3-yl)-amide

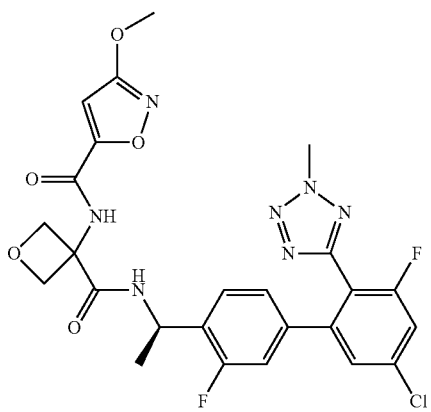 [SMILES: COc1cc(C(=O)NC2(C(=O)N[C@H](C)c3ccc(-c4cc(Cl)cc(F)c4-c4nnn(C)n4)cc3F)COC2)on1]

The title compound was prepared in analogy to example 1 using intermediate 5 instead of intermediate 1 and 3-methoxy-isoxazole-5-carboxylic acid (intermediate 14) instead of 3-fluoro-5-(trifluoromethyl)benzoic acid and was obtained as white solid. MS: 572.2 [M−H]⁻.

Example 44

2-Methoxy-pyrimidine-5-carboxylic acid (3-{(R)-1-[5'-chloro-3,3'-difluoro-2'-(2-methyl-2H-tetrazol-5-yl)-biphenyl-4-yl]-ethylcarbamoyl}-oxetan-3-yl)-amide

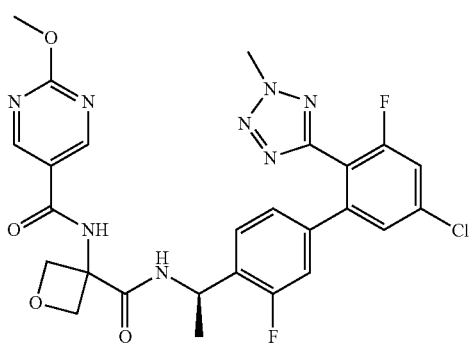 [SMILES: COc1ncc(C(=O)NC2(C(=O)N[C@H](C)c3ccc(-c4cc(Cl)cc(F)c4-c4nnn(C)n4)cc3F)COC2)cn1]

The title compound was prepared in analogy to example 1 using intermediate 5 instead of intermediate 1 and 2-methoxy-pyrimidine-5-carboxylic acid instead of 3-fluoro-5-(trifluoromethyl)benzoic acid and was obtained as white solid. MS: 585.1 [M+H]⁺.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound according to formula (I):

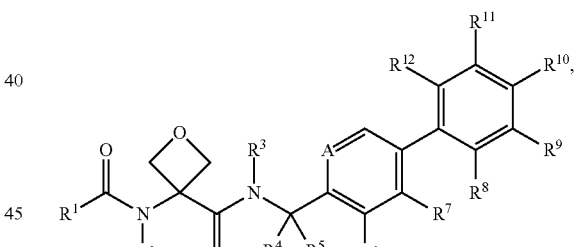

(I)

wherein:
$R^1$ is isoxazolyl, optionally substituted with lower alkyl or alkoxy;
$R^2$ is selected from the group consisting of hydrogen, alkyl and cycloalkyl;
$R^3$ is selected from the group consisting of hydrogen, alkyl and cycloalkyl;
$R^4$ is selected from the group consisting of hydrogen, alkyl and cycloalkyl;
$R^5$ is selected from the group consisting of hydrogen, alkyl and cycloalkyl;
or $R^4$ and $R^5$ together form a cycloalkyl with the carbon they are attached to;
$R^6$ is selected from the group consisting of hydrogen and halogen;
$R^7$ is hydrogen;
$R^8$ is alkyloxadiazolyl;
$R^9$ is selected from the group consisting of hydrogen and halogen;

$R^{10}$ is hydrogen;
$R^{11}$ is selected from the group consisting of hydrogen and halogen;
$R^{12}$ is hydrogen;
$R^{13}$ is selected from the group consisting of hydrogen and halogen;
A is N; and
wherein one of $R^4$ and $R^5$ is hydrogen and the other is alkyl, or a pharmaceutically acceptable salt thereof.

2. A compound according to claim 1, wherein $R^4$ and $R^5$ together form a cycloalkyl with the carbon they are attached to.

3. The compound according to claim 1, selected from the group consisting of:
  Isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide; and
  3-Methyl-isoxazole-5-carboxylic acid [3-((R)-1-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide;
  or a pharmaceutically acceptable salt thereof.

4. A pharmaceutical composition comprising a compound according to claim 1 and a therapeutically inert carrier.

5. The compound of claim 1 wherein said compound is 3-methyl-isoxazole-5-carboxylic acid [31-{5-[5-chloro-3-fluoro-2-(5-methyl-[1,2,4]oxadiazol-3-yl)-phenyl]-3-fluoro-pyridin-2-yl}-ethylcarbamoyl)-oxetan-3-yl]-amide or a pharmaceutically acceptable salt thereof.

* * * * *